US008048422B2

(12) United States Patent
Burkly et al.

(10) Patent No.: US 8,048,422 B2
(45) Date of Patent: Nov. 1, 2011

(54) TWEAK BINDING ANTIBODIES

(75) Inventors: Linda C. Burkly, West Newton, MA (US); Ellen Garber, Cambridge, MA (US); Alexey Lugovsky, Woburn, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 666 days.

(21) Appl. No.: 11/944,709

(22) Filed: Nov. 26, 2007

(65) Prior Publication Data

US 2008/0241163 A1 Oct. 2, 2008

Related U.S. Application Data

(63) Continuation of application No. PCT/US2006/019706, filed on May 25, 2006.

(60) Provisional application No. 60/685,149, filed on May 27, 2005.

(51) Int. Cl.
*A61K 39/395* (2006.01)
*C07K 16/24* (2006.01)

(52) U.S. Cl. .............. 424/158.1; 530/388.23; 530/387.1

(58) Field of Classification Search ........................ None
See application file for complete search history.

(56) References Cited

U.S. PATENT DOCUMENTS

| | | | |
|---|---|---|---|
| 5,223,409 A | 6/1993 | Ladner et al. |
| 5,225,539 A | 7/1993 | Winter |
| 5,624,821 A | 4/1997 | Winter et al. |
| 5,648,260 A | 7/1997 | Winter et al. |
| 5,693,762 A | 12/1997 | Queen |
| 5,859,205 A | 1/1999 | Adair |
| 5,885,793 A | 3/1999 | Griffiths et al. |
| 6,207,642 B1 | 3/2001 | Wiley |
| 6,300,064 B1 | 10/2001 | Knappik et al. |
| 6,407,213 B1 | 6/2002 | Carter et al. |
| 6,727,225 B2 | 4/2004 | Wiley |
| 6,824,773 B2 | 11/2004 | Wiley |
| 6,943,146 B2 | 9/2005 | Jakubowski et al. |
| 7,087,725 B2 | 8/2006 | Browning et al. |
| 7,109,298 B2 | 9/2006 | Browning et al. |
| 7,129,061 B1 | 10/2006 | Browning et al. |
| 7,169,387 B2 | 1/2007 | Rennert |
| 7,208,151 B2 | 4/2007 | Browning et al. |
| 7,482,430 B2 | 1/2009 | Wiley |
| 7,495,086 B2 | 2/2009 | Kim et al. |
| 7,507,807 B2 | 3/2009 | Wiley |
| 7,517,962 B2 | 4/2009 | Wiley |
| 7,566,769 B2 | 7/2009 | Browning et al. |
| 7,579,001 B2 | 8/2009 | Rennert |
| 7,695,934 B2 | 4/2010 | Browning |
| 7,731,963 B2 | 6/2010 | Browning |
| 2002/0015703 A1 | 2/2002 | Rennert |
| 2005/0007957 A1 | 1/2005 | Ibaraki et al. |
| 2005/0008625 A1 | 1/2005 | Balint et al. |
| 2005/0008636 A1 | 1/2005 | Rennert |
| 2006/0003932 A1 | 1/2006 | Jakubowski et al. |
| 2006/0240004 A1 | 10/2006 | Burkly et al. |
| 2006/0252122 A1 | 11/2006 | Browning et al. |
| 2007/0110745 A1 | 5/2007 | Rennert |
| 2007/0280940 A1 | 12/2007 | Winkles et al. |
| 2008/0008714 A1 | 1/2008 | Browning et al. |
| 2008/0187544 A1 | 8/2008 | Burkly et al. |
| 2008/0279853 A1 | 11/2008 | Burkly et al. |
| 2008/0286271 A1 | 11/2008 | Ashkenazi et al. |
| 2008/0292622 A1 | 11/2008 | Burkly et al. |
| 2009/0068102 A1 | 3/2009 | Burkly et al. |
| 2009/0124993 A1 | 5/2009 | Burkly et al. |
| 2009/0311313 A1 | 12/2009 | Burkly et al. |
| 2010/0061985 A1 | 3/2010 | Rennert |

FOREIGN PATENT DOCUMENTS

| | | |
|---|---|---|
| EP | 1566636 A1 | 8/2005 |
| WO | WO 98/05783 A1 | 2/1998 |
| WO | WO 98/35061 A2 | 8/1998 |
| WO | WO 98/52976 A1 | 11/1998 |
| WO | WO 99/19490 A1 | 4/1999 |
| WO | WO 00/34317 A2 | 6/2000 |
| WO | WO 00/42073 A1 | 7/2000 |
| WO | WO 01/45730 A2 | 6/2001 |
| WO | WO 02/22166 A2 | 3/2002 |
| WO | WO 03/086311 A2 | 10/2003 |
| WO | WO 2005/080972 A1 | 9/2005 |
| WO | WO 2006/047172 A1 | 5/2006 |
| WO | WO 2006/052926 A2 | 5/2006 |
| WO | WO 2006/088890 A2 | 8/2006 |
| WO | WO 2006/089095 A2 | 8/2006 |
| WO | WO 2006/096487 A2 | 9/2006 |
| WO | WO 2006/122187 A2 | 11/2006 |
| WO | WO 2006/130429 A2 | 12/2006 |
| WO | WO 2006/138219 A2 | 12/2006 |
| WO | WO 2008/048924 A2 | 4/2008 |

OTHER PUBLICATIONS

Portolano et al. Lack of promiscuity in autoantigen-specific H and L chain combinations as revealed by Human H an L chain "Roulette". J. Immunol. vol. 150(3):880-887 (1993).*
Clackson et al. Making antibody fragments using phage display libraries. Nature. vol. 352:624-628 (1991).*
Pascalis et al. Grafting of "Abbreviated" Complementarity-determining regions containing specificity-determining residues essential for ligand contact to engineer a less immunogenic humanized monoclonal antibody. The Journal of Immunology, 169:3076-3084 (2002.).*
Bose et al. Problems in using statistical analysis of replacement and silent mutations in antibody genes for determining antigen-driven affinity selection. Immunology, vol. 116:172-183 (2005).*
David et al. A study of the structural correlates of affinity maturation: Antibody affinity as a function of chemical interactions, structural plasticity and stability. Molecular Immunology, vol. 44:1342-1351 (2007).*

(Continued)

*Primary Examiner* — Marianne P Allen
*Assistant Examiner* — Regina M Deberry
(74) *Attorney, Agent, or Firm* — Finnegan, Henderson, Farabow, Garrett & Dunner, L.L.P.

(57) ABSTRACT

Anti-Tweak antibodies are described.

4 Claims, No Drawings

OTHER PUBLICATIONS

Clark et al. Trends in antibody sequence changes during the somatic hypermutation process. The Journal of Immunology, vol. 177:333-340 (2006).*

Angal et al., "A single amino acid substitution abolishes the heterogeneity of chimeric mouse/human (IgG4) antibody", Mol. Immunol. 30:105-108 (1993).

Boucraut, J. et al., "Anti-TWEAK Monoclonal Antibodies Reduce CNS Immune Cell Infiltration and Severity of Experimental Autoimmune Encephalomyelitis" Meeting: Autoimmunity: Mechanisms and Novel Treatments, Mykonos, Greece, Oct. 8-13, 2003; Aegean Conference Series, vol. 12:Abstract 64, p. 89 (2003).

Campbell, S. et al., "Proinflammatory Effects of TWEAK/Fn14 Interactions in Glomerular Mesangial Cells", J. Immunol. 176:1889-1898 (2006).

Campbell, S. et al., "The Role of Tweak/Fn14 in the Pathogenesis of Inflammation and Systemic Autoimmunity", Frontiers in Bioscience 9:2273-2284 (2004).

Chicheportiche, Y. et al., "Proinflammatory Activity of TWEAK on Human Dermal Fibroblasts and Synoviocytes: Blocking and Enhancing Effects of Anti-TWEAK Monoclonal Antibodies", Arthritis Res. 4(2):126-33 (2002). Epub Nov. 9, 2001.

Chothia et al., "Structural repertoire of the human VH segments", J. Mol. Biol. 227:799-817 (1992).

Davies et al., "Single antibody domains as small recognition units: design and in vitro antigen selection of camelized, human VH domains with improved protein stability", Protein Eng. 9(6):531-537 (1996).

Desplat-Jego, S. et al., "Anti-TWEAK monoclonal antibodies reduce immune cell infiltration in the central nervous system and severity of experimental autoimmune encephalomyelitis", Clin. Immunol. 117(1):15-23 (2005).

Desplat-Jego, S. et al., "TWEAK Is Expressed by Glial Cells, Induces Astrocyte Proliferation and Increases EAE Severity", J. Neuroimmunol. 133:116-123 (2002).

Donahue, P.J. et al., "TWEAK Is an Endothelial Cell Growth and Chemotactic Factor That Also Potentiates FGF-2 and VEGF-A Mitogenic Activity", Arterioscler. Thromb. Vasc. Biol. 23:594-600 (2003).

Feng, S-L. Y., et al., "The Fn14 Immediate-Early Response Gene Is Induced During Liver Regeneration and Highly Expressed in Both Human and Murine Hepatocellular Carcinomas", Am. J. Pathol. 156(4):1253-1261 (2000).

Hahm, K. et al., "TWEAK overexpression induces hyperplasia in liver and kidney", FASEB J. 17:Abstract No. 471.5 (2003).

Han, H. et al., "Overexpression of FN14/TEAK receptor in pancreatic cancer", Proc. Am. Assoc. Cancer Res Annual Meeting 46(Suppl. S):Abstract No. 2363 (Apr. 18, 2005).

Ho, D.H. et al., "Soluble Tumor Necrosis Factor-Like Weak Inducer of Apoptosis Overexpression in HEK293 Cells Promotes Tumor Growth and Angiogenesis in Athymic Nude Mice", Cancer Res. 64:8968-8972 (Dec. 15, 2004).

Jakubowski, A. et al., "Dual role for TWEAK in angiogenic regulation", J. Cell Sci. 115(Pt 2):267-274 (Jan. 15, 2002).

Jakubowski, A. et al., "TWEAK induces liver progenitor cell proliferation", J. Clin. Invest. 115(9):2330-2340 (Sep. 2005).

Jakubowski, A. et al., "TWEAK Synergizes With Basis Fibroblast Growth Factor to Induce Endothelial Cell Proliferation, Migration and Lumen Morphogenesis", Abstracts for the 8th International TNF Congress on Tumor Necrosis Factor and Related Cytokines, Scand. J. Immunol. 51(Supplement 1): 62 (2000).

Kawakita, T. et al., "Functional expression of TWEAK in human hepatocellular carcinoma: possible implication in cell proliferation and tumor angiogenesis", Biochem. Biophys. Res. Commun. 318:726-733 (2004).

Lund et al., "Human Fc gamma RI and Fc gamma RII interact with distinct but overlapping sites on human IgG.", J. Immun. 147:2657-2662 (1991).

Lynch, C. et al., "TWEAK Induces Proliferation in Endothelial Cells and Substitutes for EGF and Hydrocortisone in Culture", J. Interferon Cytokine Res. 18:A-46 (1998).

Lynch, C.N. et al., "TWEAK Induces Angiogenesis and Proliferation of Endothelial Cells", J. Biol. Chem. 274(13):8455-8459 (1999).

Michaelson, J.S. et al., "Tweak induces mammary epithelial branching morphogenesis", Oncogene 24:2613-2624 (2005).

Morgan, A. et al., "The N-terminal end of the CH2 domain of chimeric human IgG1 anti-HLA-DR is necessary for C1q, Fc gamma RI and Fc gamma RIII binding", Immunology 86:319-324 (1995).

Mueller, A.M. et al., "Targeting fibroblast growth-factor-inducible-14 signaling protects from chronic relapsing experimental autoimmune encephalomyelitis", J. Neuroimmunol. 159(1-2):55-65 (2005).

Nakayama, M. et al., "Involvement of Tweak in Interferon γ-Stimulated Monocyte Cytotoxicity" J Exp Med. 192(9):1373-1380 (Nov. 6, 2000).

Nakayama, M. et al., "Characterization of murine TWEAK and its receptor (Fn14) by monoclonal antibodies", Biochem. Biophys. Res. Commun. 306(4):819-25 (Jul. 11, 2003).

Perper, S.J. et al., "TWEAK is a novel arthritogenic mediator", J. Immunol. 177(4):2610-2620 (Aug. 15, 2006).

Potrovita, I. et al., "Tumor Necrosis Factor-Like Weak Inducer of Apoptosis-Induced Neurodegeneration", J. Neurosci. 24(38):8237-8244 (Sep. 22, 2004).

Potrovita, I. et al., "TWEAK—A Regulator of Neuronal Cell Death", Naunyn-Schmiedeberg's Archives of Pharmacology 369(Suppl. 1):R12 (Mar. 9, 2004).

Putterman, C. et al., "Tweak Blockade Improves Kidney Disease in Lupus-Prone Mice: A Novel Approach to the Treatment of Lupus Nephritis?", FASEB J., Experimental Biology 2004, Abstracts Part II, 18(5):Abstract No. 562.27 (2004).

Saas, P. et al., "TWEAK Stimulation of Astrocytes and the Proinflammatory Consequences", GLIA 32(1):102-107 (2000).

Tomlinson et al., "The repertoire of human germline VH sequences reveals about fifty groups of VH segments with different hypervariable loops", J. Mol. Biol. 227:776-798 (1992).

Tomlinson, I.M. et al., "The structural repertoire of the human V kappa domain" EMBO J. 14:4628 (1995).

Tran, N.L. et al., "The Human Fn14 Receptor Gene Is Up-Regulated in Migrating Glioma Cells in Vitro and Overexpressed in Advanced Glial Tumors", Am. J. Pathol. 162(4):1313-1321 (Apr. 2003).

Tran, N.L. et al., "The Tumor Necrosis Factor-like Weak Inducer of Apoptosis (TWEAK)-Fibroblast Growth Factor-inducible 14 (Fn14) Signaling System Regulates Glioma Cell Survival via NFkappaB Pathway Activation and BCL-XL/BCL-W Expression", J. Biol. Chem.280(5):3483-3492 (Feb. 4, 2005).

Trauth et al., "Monoclonal Anitbody-Mediated Tumor Regression by Induction of Apoptosis", Science 245:301-305 (1989).

Wiley, S.R. et al., "A Novel TNF Receptor Family Member Binds TWEAK and Is implicated in Angiogenesis", Immunity 15:837-846 (2001).

Wiley, S.R. et al., "TWEAK, a member of the TNF superfamily, is a multifunctional cytokine that binds the TweakR/Fn14 receptor", Cytokine & Growth Factor Reviews 14:241-249 (2003).

Winkles, J.A. et al., "Role of TWEAK and Fn14 in tumor biology", Frontiers in Bioscience 12:2761-2771 (Jan. 1, 2007).

Winkles, J.A. et al., "TWEAK and Fn14: New molecular targets for cancer therapy?", Cancer Letters 235:11-17 (2006).

Zhao, Z. et al., "TWEAK/Fn14 Interactions Are Instrumental in the Pathogenesis of Nephritis in the Chronic Graft-versus-Host Model of Systemic Lupus Erythematosis", J. Immunol. 179:7949-7958 (2007).

* cited by examiner

SEQUENCE LISTING

```
<160> NUMBER OF SEQ ID NOS: 69

<210> SEQ ID NO 1
<211> LENGTH: 10
<212> TYPE: PRT
<213> ORGANISM: Mus musculus

<400> SEQUENCE: 1

Gly Phe Thr Phe Ser Arg Tyr Ala Met Ser
1               5                   10

<210> SEQ ID NO 2
<211> LENGTH: 17
<212> TYPE: PRT
<213> ORGANISM: Mus musculus

<400> SEQUENCE: 2

Glu Ile Ser Ser Gly Gly Ser Tyr Pro Tyr Tyr Pro Asp Thr Val Thr
1               5                   10                  15

Gly

<210> SEQ ID NO 3
<211> LENGTH: 16
<212> TYPE: PRT
<213> ORGANISM: Mus musculus

<400> SEQUENCE: 3

Val Leu Tyr Tyr Asp Tyr Asp Gly Asp Arg Ile Glu Val Met Asp Tyr
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Tyr or Phe
<220> FEATURE:
<221> NAME/KEY: VARIANT
<222> LOCATION: 3
<223> OTHER INFORMATION: Xaa = Asn or Thr
<220> FEATURE:
<221> NAME/KEY: VARIANT
<222> LOCATION: 5
<223> OTHER INFORMATION: Xaa = Ser, Thr, Asp or Asn
<220> FEATURE:
<221> NAME/KEY: VARIANT
<222> LOCATION: 6
<223> OTHER INFORMATION: Xaa = Arg or Tyr
<220> FEATURE:
<221> NAME/KEY: VARIANT
<222> LOCATION: 9
<223> OTHER INFORMATION: xaa = Met, Ile or Leu
<220> FEATURE:
<221> NAME/KEY: VARIANT
```

```
<222> LOCATION: 10
<223> OTHER INFORMATION: Xaa = His or Ser

<400> SEQUENCE: 4

Gly Xaa Xaa Phe Xaa Xaa Tyr Ala Xaa Xaa
 1               5                  10

<210> SEQ ID NO 5
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Pro or Val
<220> FEATURE:
<221> NAME/KEY: VARIANT
<222> LOCATION: 5
<223> OTHER INFORMATION: Xaa = Thr or Ser
<220> FEATURE:
<221> NAME/KEY: VARIANT
<222> LOCATION: 7
<223> OTHER INFORMATION: Xaa = Thr or Lys

<400> SEQUENCE: 5

Tyr Tyr Xaa Asp Xaa Val Xaa Gly
 1               5

<210> SEQ ID NO 6
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Val or Leu
<220> FEATURE:
<221> NAME/KEY: VARIANT
<222> LOCATION: 2
<223> OTHER INFORMATION: Xaa = Ile or Leu
<220> FEATURE:
<221> NAME/KEY: VARIANT
<222> LOCATION: 3, 4, 6
<223> OTHER INFORMATION: Xaa = Tyr or Phe

<400> SEQUENCE: 6

Xaa Xaa Xaa Xaa Asp Xaa Asp
 1               5

<210> SEQ ID NO 7
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2
<223> OTHER INFORMATION: Xaa = Arg or Lys
<220> FEATURE:
<221> NAME/KEY: VARIANT
<222> LOCATION: 3
<223> OTHER INFORMATION: Xaa = Ile, Leu, Val or Met
<220> FEATURE:
<221> NAME/KEY: VARIANT
<222> LOCATION: 4
```

```
<223> OTHER INFORMATION: Xaa = Glu, Gln or Asp
<220> FEATURE:
<221> NAME/KEY: VARIANT
<222> LOCATION: 5
<223> OTHER INFORMATION: Val, Ala or Leu
<220> FEATURE:
<221> NAME/KEY: VARIANT
<222> LOCATION: 7
<223> OTHER INFORMATION: Xaa = Asp or Glu

<400> SEQUENCE: 7

Xaa Xaa Xaa Xaa Xaa Met Xaa
 1               5

<210> SEQ ID NO 8
<211> LENGTH: 16
<212> TYPE: PRT
<213> ORGANISM: Mus musculus

<400> SEQUENCE: 8

Arg Ser Ser Gln Ser Leu Val Ser Ser Lys Gly Asn Thr Tyr Leu His
 1               5                  10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
 1               5

<210> SEQ ID NO 10
<211> LENGTH: 9
<212> TYPE: PRT
<213> ORGANISM: Mus musculus

<400> SEQUENCE: 10

Ser Gln Ser Thr His Phe Pro Arg Thr
 1               5

<210> SEQ ID NO 11
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 6
<223> OTHER INFORMATION: Xaa = Leu or Ile
<220> FEATURE:
<221> NAME/KEY: VARIANT
<222> LOCATION: 7
<223> OTHER INFORMATION: Xaa = Lys or Val
<220> FEATURE:
<221> NAME/KEY: VARIANT
<222> LOCATION: 10
<223> OTHER INFORMATION: Xaa = Lys or Arg
<220> FEATURE:
<221> NAME/KEY: VARIANT
<222> LOCATION: 13
<223> OTHER INFORMATION: Xaa = Thr or Asn
<220> FEATURE:
<221> NAME/KEY: VARIANT
<222> LOCATION: 16
<223> OTHER INFORMATION: Xaa = Glu, His, Asp, Asn, Gln or Tyr
```

```
<400> SEQUENCE: 11

Xaa Ser Ser Gln Ser Xaa Xaa Ser Ser Xaa Gly Asn Xaa Tyr Leu Xaa
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 6
<223> OTHER INFORMATION: Xaa = Leu or Ile
<220> FEATURE:
<221> NAME/KEY: VARIANT
<222> LOCATION: 10
<223> OTHER INFORMATION: Xaa = Lys or Arg
<220> FEATURE:
<221> NAME/KEY: VARIANT
<222> LOCATION: 13
<223> OTHER INFORMATION: Xaa = Thr or Asn

<400> SEQUENCE: 12

Xaa Ser Ser Gln Ser Xaa Val Ser Ser Xaa Gly Asn Xaa Tyr Leu His
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Lys or Glu
<220> FEATURE:
<221> NAME/KEY: VARIANT
<222> LOCATION: 2
<223> OTHER INFORMATION: Xaa = Leu, Val or Ile
<220> FEATURE:
<221> NAME/KEY: VARIANT
<222> LOCATION: 4
<223> OTHER INFORMATION: Xaa = Asn, Tyr or Ser
<220> FEATURE:
<221> NAME/KEY: VARIANT
<222> LOCATION: 5
<223> OTHER INFORMATION: Xaa = Arg or Trp
<220> FEATURE:
<221> NAME/KEY: VARIANT
<222> LOCATION: 6
<223> OTHER INFORMATION: Xaa = Phe, Ala or Asp

<400> SEQUENCE: 13

Xaa Xaa Ser Xaa Xaa Xaa Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Leu, Val or Ile
<220> FEATURE:
<221> NAME/KEY: VARIANT
```

```
<222> LOCATION: 4
<223> OTHER INFORMATION: Xaa = Asn, Tyr or Ser
<220> FEATURE:
<221> NAME/KEY: VARIANT
<222> LOCATION: 6
<223> OTHER INFORMATION: Xaa = Phe, Ala or Asp

<400> SEQUENCE: 14

Lys Xaa Ser Xaa Arg Xaa Ser
 1               5

<210> SEQ ID NO 15
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ser or Met
<220> FEATURE:
<221> NAME/KEY: VARIANT
<222> LOCATION: 3
<223> OTHER INFORMATION: Xaa = Gly, Ser or Ala
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 5
<223> OTHER INFORMATION: Xaa = His, Glu or Gln
<220> FEATURE:
<221> NAME/KEY: VARIANT
<222> LOCATION: 6
<223> OTHER INFORMATION: Xaa = Phe, Trp or Leu

<400> SEQUENCE: 15

Xaa Gln Xaa Xaa Xaa Xaa Pro
 1               5

<210> SEQ ID NO 16
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Gly, Ser or Ala
<220> FEATURE:
<221> NAME/KEY: VARIANT
<222> LOCATION: 4
<223> OTHER INFORMATION: Xaa = Ser, Ile or Thr
<220> FEATURE:
<221> NAME/KEY: VARIANT
<222> LOCATION: 5
<223> OTHER INFORMATION: Xaa = His, Glu or Gln

<400> SEQUENCE: 16

Ser Gln Xaa Xaa Xaa Phe Pro
 1               5

<210> SEQ ID NO 17
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 17
```

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 18
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 19
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Ser Ser
            20                  25                  30

Lys Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 20
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 20

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Ser Ser
            20                  25                  30

Lys Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 21
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 21

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 22
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 22

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val Ser Ser
            20                  25                  30

```
Lys Gly Asn Thr Tyr Leu His Trp Tyr Leu Gln Lys Pro Gly Gln Pro
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 23
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 23

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 24
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 25
```

<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 25

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Ser Ser
            20                  25                  30

Lys Gly Asn Thr Tyr Leu His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr
            100

<210> SEQ ID NO 26
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val Ser Ser
            20                  25                  30

Lys Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Phe Pro Arg Thr
            100

<210> SEQ ID NO 27
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Tyr
            20                  25                  30

Ala Met Ser Trp Val Arg Gln Ala Pro Gly Gln Gly Leu Glu Trp Met
        35                  40                  45

Gly Glu Ile Ser Ser Gly Gly Ser Tyr Pro Tyr Tyr Pro Asp Thr Val

```
                  50                  55                  60
Thr Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Val Leu Tyr Tyr Asp Tyr Asp Gly Asp Arg Ile Glu
                100                 105                 110

<210> SEQ ID NO 28
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 28

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Ser Arg Tyr
                20                  25                  30

Ala Met Ser Trp Val Arg Gln Ala Pro Gly Gln Arg Leu Glu Trp Met
            35                  40                  45

Gly Glu Ile Ser Ser Gly Gly Ser Tyr Pro Tyr Tyr Pro Asp Thr Val
        50                  55                  60

Thr Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Leu Tyr Tyr Asp Tyr Asp Gly Asp Arg Ile Glu
                100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 29

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Ser Arg Tyr
                20                  25                  30

Ala Met Ser Trp Val Arg Gln Ala Thr Gly Gln Gly Leu Glu Trp Met
            35                  40                  45

Gly Glu Ile Ser Ser Gly Gly Ser Tyr Pro Tyr Tyr Pro Asp Thr Val
        50                  55                  60

Thr Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Leu Tyr Tyr Asp Tyr Asp Gly Asp Arg Ile Glu
                100                 105                 110

<210> SEQ ID NO 30
<211> LENGTH: 110
<212> TYPE: PRT
<213> ORGANISM: Artificial Sequence
<220> FEATURE:
<223> OTHER INFORMATION: Synthetically generated peptide
```

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Tyr
            20                  25                  30

Ala Met Ser Trp Val Arg Gln Ala Pro Gly Gln Gly Leu Glu Trp Met
        35                  40                  45

Gly Glu Ile Ser Ser Gly Gly Ser Tyr Pro Tyr Tyr Pro Asp Thr Val
    50                  55                  60

Thr Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Leu Tyr Tyr Asp Tyr Asp Gly Asp Arg Ile Glu
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Phe Ser Arg Tyr
            20                  25                  30

Ala Met Ser Trp Val Arg Gln Ala Pro Gly Lys Gly Leu Glu Trp Met
        35                  40                  45

Gly Glu Ile Ser Ser Gly Gly Ser Tyr Pro Tyr Tyr Pro Asp Thr Val
    50                  55                  60

Thr Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Val Leu Tyr Tyr Asp Tyr Asp Gly Asp Arg Ile Glu
            100                 105                 110

<210> SEQ ID NO 32
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 32

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Ser Arg Tyr
            20                  25                  30

Ala Met Ser Trp Val Arg Gln Ala Pro Gly Gln Ala Leu Glu Trp Met
        35                  40                  45

Gly Glu Ile Ser Ser Gly Gly Ser Tyr Pro Tyr Tyr Pro Asp Thr Val
    50                  55                  60

Thr Gly Arg Val Thr Ile Thr Arg Asp Arg Ser Met Ser Thr Ala Tyr
65                  70                  75                  80

```
Met Glu Leu Ser Ser Leu Arg Ser Glu Asp Thr Ala Met Tyr Tyr Cys
                85                  90                  95

Ala Arg Val Leu Tyr Tyr Asp Tyr Asp Gly Asp Arg Ile Glu
            100                 105                 110

<210> SEQ ID NO 33
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Tyr
                20                  25                  30

Ala Met Ser Trp Val Arg Gln Ala Pro Gly Gln Gly Leu Glu Trp Met
            35                  40                  45

Gly Glu Ile Ser Ser Gly Gly Ser Tyr Pro Tyr Tyr Pro Asp Thr Val
        50                  55                  60

Thr Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Leu Tyr Tyr Asp Tyr Asp Gly Asp Arg Ile Glu
            100                 105                 110

<210> SEQ ID NO 34
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 34

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Ser Arg Tyr
                20                  25                  30

Ala Met Ser Trp Val Arg Gln Arg Gln Arg Leu Glu Trp Ile Gly Glu
            35                  40                  45

Ile Ser Ser Gly Gly Ser Tyr Pro Tyr Tyr Pro Asp Thr Val Thr Gly
        50                  55                  60

Arg Val Thr Ile Thr Arg Asp Met Ser Thr Ser Thr Ala Tyr Met Glu
65                  70                  75                  80

Leu Ser Ser Leu Arg Ser Glu Asp Thr Ala Val Tyr Tyr Cys Ala Ala
                85                  90                  95

Val Leu Tyr Tyr Asp Tyr Asp Gly Asp Arg Ile Glu
            100                 105

<210> SEQ ID NO 35
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 35

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
             20                  25                  30

Ala Met Ser Trp Val Arg Gln Ala Pro Gly Lys Gly Leu Glu Trp Val
         35                  40                  45

Ala Glu Ile Ser Ser Gly Gly Ser Tyr Pro Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Tyr Tyr Asp Tyr Asp Gly Asp Arg Ile Glu
            100                 105                 110
```

<210> SEQ ID NO 36
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 36

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Ser Arg Tyr
             20                  25                  30

Ala Met Ser Trp Val Arg Gln Ala Pro Gly Lys Gly Leu Glu Trp Val
         35                  40                  45

Ser Glu Ile Ser Ser Gly Gly Ser Tyr Pro Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Val Leu Tyr Tyr Asp Tyr Asp Gly Asp Arg Ile Glu
            100                 105                 110
```

<210> SEQ ID NO 37
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 37

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Arg Tyr
             20                  25                  30

Ala Met Ser Trp Ile Arg Gln Ala Pro Gly Lys Gly Leu Glu Trp Val
         35                  40                  45

Ser Glu Ile Ser Ser Gly Gly Ser Tyr Pro Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Tyr Tyr Asp Tyr Asp Gly Asp Arg Ile Glu
            100                 105                 110
```

<210> SEQ ID NO 38
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 38

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Gly Glu Ile Ser Ser Gly Gly Ser Tyr Pro Tyr Tyr Pro Asp Thr Val
    50                  55                  60

Thr Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Val Leu Tyr Tyr Asp Tyr Asp Gly Asp Arg Ile Glu
            100                 105                 110
```

<210> SEQ ID NO 39
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 39

```
Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Val Leu Tyr Tyr Asp Tyr Asp Gly Asp Arg Ile Glu
            100                 105                 110
```

<210> SEQ ID NO 40
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 40

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
```

```
                35                  40                  45
Ser Glu Ile Ser Ser Gly Gly Ser Tyr Pro Tyr Tyr Pro Asp Thr Val
 50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Tyr Tyr Asp Tyr Asp Gly Asp Arg Ile Glu
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 41

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Ala Met Ser Trp Val Arg Gln Ala Pro Gly Lys Gly Leu Glu Trp Val
         35                  40                  45

Ser Glu Ile Ser Ser Gly Gly Ser Tyr Pro Tyr Tyr Pro Asp Thr Val
 50                  55                  60

Thr Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Tyr Tyr Asp Tyr Asp Gly Asp Arg Ile Glu
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 42

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Arg Tyr
             20                  25                  30

Ala Met Ser Trp Val Arg Gln Ala Pro Gly Lys Gly Leu Glu Trp Val
         35                  40                  45

Ala Glu Ile Ser Ser Gly Gly Ser Tyr Pro Tyr Tyr Pro Asp Thr Val
 50                  55                  60

Thr Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Tyr Tyr Asp Tyr Asp Gly Asp Arg Ile Glu
            100                 105                 110

<210> SEQ ID NO 43
<211> LENGTH: 110
<212> TYPE: PRT
```

<213> ORGANISM: Artificial Sequence
<220> FEATURE:
<223> OTHER INFORMATION: Synthetically generated peptide

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu
            100                 105                 110

<210> SEQ ID NO 44
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 44

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Tyr Tyr Asp Tyr Asp Gly Asp Arg Ile Glu
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 45

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu
            100                 105                 110

<210> SEQ ID NO 46
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 46

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Glu Ile Ser Ser Gly Gly Ser Tyr Pro Tyr Tyr Pro Asp Thr Val
50                  55                  60

Thr Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Val Leu Tyr Tyr Asp Tyr Asp Gly Asp Arg Ile Glu
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Glu Ile Ser Ser Gly Gly Ser Tyr Pro Tyr Tyr Pro Asp Thr Val
50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Leu Tyr Tyr Asp Tyr Asp Gly Asp Arg Ile Glu
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 48

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Arg Tyr
            20                  25                  30

Ala Met Ser Trp Phe Arg Gln Ala Pro Gly Lys Gly Leu Glu Trp Val
        35                  40                  45

Gly Glu Ile Ser Ser Gly Gly Ser Tyr Pro Tyr Tyr Pro Asp Thr Val
    50                  55                  60

Thr Gly Arg Phe Thr Ile Ser Arg Asp Gly Ser Lys Ser Ile Ala Tyr
65                  70                  75                  80

Leu Gln Met Asn Ser Leu Lys Thr Glu Asp Thr Ala Val Tyr Tyr Cys
                85                  90                  95

Thr Arg Val Leu Tyr Tyr Asp Tyr Asp Gly Asp Arg Ile Glu
            100                 105                 110

<210> SEQ ID NO 49
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Tyr Val
        35                  40                  45

Ser Glu Ile Ser Ser Gly Gly Ser Tyr Pro Tyr Tyr Pro Asp Thr Val
    50                  55                  60

Thr Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Val Leu Tyr Tyr Asp Tyr Asp Gly Asp Arg Ile Glu
            100                 105                 110

<210> SEQ ID NO 50
<211> LENGTH: 125
<212> TYPE: PRT
<213> ORGANISM: Mus musculus

<400> SEQUENCE: 50

Glu Val Gln Leu Val Glu Ser Gly Gly Gly Leu Val Arg Pro Gly Gly
1               5                   10                  15

Ser Leu Lys Leu Phe Cys Ala Ala Ser Gly Phe Thr Phe Ser Arg Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Lys Ser Glu Asp Thr Ala Met Tyr Tyr Cys
                85                  90                  95

Ala Arg Val Leu Tyr Tyr Asp Tyr Asp Gly Asp Arg Ile Glu Val Met 100                 105                 110

Asp Tyr Trp Gly Gln Gly Thr Ala Val Ile Val Ser Ser
        115                 120                 125

<210> SEQ ID NO 51
<211> LENGTH: 112
<212> TYPE: PRT
<213> ORGANISM: Mus musculus

<400> SEQUENCE: 51

Asp Val Val Met Thr Gln Ser Pro Leu Ser Leu Ser Val Ser Leu Gly
1               5                   10                  15

Asp Gln Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Ala Ala Glu Asp Leu Gly Val Tyr Phe Cys Ser Gln Ser
                85                  90                  95

Thr His Phe Pro Arg Thr Phe Gly Gly Gly Thr Thr Leu Glu Ile Lys
            100                 105                 110

<210> SEQ ID NO 52
<211> LENGTH: 125
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Asp Pro Met Thr Thr Val Val Lys Pro Ser Leu Ala Thr Asn
            100                 105                 110

Asp Tyr Trp Gly Gln Gly Thr Leu Val Thr Val Ser Ser
        115                 120                 125

<210> SEQ ID NO 53
<211> LENGTH: 112
<212> TYPE: PRT
<213> ORGANISM: Homo sapiens

<400> SEQUENCE: 53

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 54
<211> LENGTH: 125
<212> TYPE: PRT
<213> ORGANISM: Mus musculus

<400> SEQUENCE: 54

```
Glu Val Gln Leu Val Glu Ser Gly Gly Gly Leu Val Arg Pro Gly Gly
 1               5                  10                  15

Ser Leu Lys Leu Phe Cys Ala Ala Ser Gly Phe Thr Phe Ser Arg Tyr
            20                  25                  30

Ala Met Ser Trp Val Arg Gln Ser Pro Glu Lys Arg Leu Glu Trp Val
            35                  40                  45

Ala Glu Ile Ser Ser Gly Gly Ser Tyr Pro Tyr Tyr Pro Asp Thr Val
 50                  55                  60

Thr Gly Arg Phe Thr Ile Ser Arg Asp Asn Ala Lys Asn Thr Leu Tyr
 65                  70                  75                  80

Leu Glu Met Ser Ser Leu Lys Ser Glu Asp Thr Ala Met Tyr Tyr Cys
                 85                  90                  95

Ala Arg Val Leu Tyr Tyr Asp Tyr Asp Gly Asp Arg Ile Glu Val Met
            100                 105                 110

Asp Tyr Trp Gly Gln Gly Thr Ala Val Ile Val Ser Ser
            115                 120                 125
```

<210> SEQ ID NO 55
<211> LENGTH: 125
<212> TYPE: PRT
<213> ORGANISM: Homo sapiens

<400> SEQUENCE: 55

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Met Thr Thr Val Val Lys Pro Ser Leu Ala Thr Asn
            100                 105                 110

Asp Tyr Trp Gly Gln Gly Thr Leu Val Thr Val Ser Ser
            115                 120                 125
```

```
<210> SEQ ID NO 56
<211> LENGTH: 112
<212> TYPE: PRT
<213> ORGANISM: Mus musculus

<400> SEQUENCE: 56

Asp Val Val Met Thr Gln Ser Pro Leu Ser Leu Ser Val Ser Leu Gly
1               5                   10                  15

Asp Gln Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Ala Ala Glu Asp Leu Gly Val Tyr Phe Cys Ser Gln Ser
                85                  90                  95

Thr His Phe Pro Arg Thr Phe Gly Gly Gly Thr Thr Leu Glu Ile Lys
            100                 105                 110

<210> SEQ ID NO 57
<211> LENGTH: 112
<212> TYPE: PRT
<213> ORGANISM: Homo sapiens

<400> SEQUENCE: 57

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 58
<211> LENGTH: 125
<212> TYPE: PRT
<213> ORGANISM: Homo sapiens

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Asp Pro Met Thr Thr Val Val Lys Pro Ser Leu Ala Thr Asn
            100                 105                 110

Asp Tyr Trp Gly Gln Gly Thr Leu Val Thr Val Ser Ser
        115                 120                 125

<210> SEQ ID NO 59
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu Val Met
            100                 105                 110

Asp Tyr Trp Gly Gln Gly Thr Leu Val Thr Val Ser Ser
        115                 120                 125

<210> SEQ ID NO 60
<211> LENGTH: 112
<212> TYPE: PRT
<213> ORGANISM: Homo sapiens

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Synthetically generated peptide

```
<400> SEQUENCE: 61

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Cys Ser Gln Ser Thr
                85                  90                  95

His Phe Pro Arg Thr Phe Gly Gly Gly Thr Lys Val Glu Ile Lys
            100                 105                 110

<210> SEQ ID NO 62
<211> LENGTH: 112
<212> TYPE: PRT
<213> ORGANISM: Homo sapiens

<400> SEQUENCE: 62

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 63

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95
```

Thr His Phe Pro Arg Thr Phe Gly Gly Gly Thr Lys Val Glu Ile Lys
            100                 105                 110

<210> SEQ ID NO 64
<211> LENGTH: 454
<212> TYPE: PRT
<213> ORGANISM: Artificial Sequence
<220> FEATURE:
<223> OTHER INFORMATION: Synthetically generated peptide

<400> SEQUENCE: 64

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu Val Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys

```
                        355                 360                 365
Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly
                450

<210> SEQ ID NO 65
<211> LENGTH: 98
<212> TYPE: PRT
<213> ORGANISM: Artificial Sequence
<220> FEATURE:
<223> OTHER INFORMATION: Synthetically generated peptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 66
<211> LENGTH: 219
<212> TYPE: PRT
<213> ORGANISM: Artificial Sequence
<220> FEATURE:
<223> OTHER INFORMATION: Synthetically generated peptide

<400> SEQUENCE: 66

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Arg Thr Phe Gly Gly Gly Thr Lys Val Glu Ile Lys
                100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 67
<211> LENGTH: 100
<212> TYPE: PRT
<213> ORGANISM: Artificial Sequence
<220> FEATURE:
<223> OTHER INFORMATION: Synthetically generated peptide

<400> SEQUENCE: 67

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro
            100
```

<210> SEQ ID NO 68
<211> LENGTH: 219
<212> TYPE: PRT
<213> ORGANISM: Artificial Sequence
<220> FEATURE:
<223> OTHER INFORMATION: Synthetically generated peptide

<400> SEQUENCE: 68

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95
```

```
Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 69
<211> LENGTH: 100
<212> TYPE: PRT
<213> ORGANISM: Artificial Sequence
<220> FEATURE:
<223> OTHER INFORMATION: Synthetically generated peptide

<400> SEQUENCE: 69

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro
            100
```

US 8,048,422 B2

TWEAK BINDING ANTIBODIES

CROSS-REFERENCE TO RELATED APPLICATIONS

This application, filed under 35 U.S.C. §111, is a continuation claiming priority under 35 U.S.C. §120 of International Application No. PCT/US2006/019706, filed on May 25, 2006, which claims priority to U.S. Application Ser. No. 60/685,149, filed on May 27, 2005. The contents of all the foregoing applications are hereby incorporated by reference.

BACKGROUND

The tumor-necrosis factor (TNF)-related cytokines are a superfamily of proteins that have an array of functions, including ones implicated in immune regulation and apoptosis regulation. TWEAK (TNF-like weak inducer of apoptosis) is one member of this superfamily.

SUMMARY

Anti-TWEAK antibodies can be used to treat a variety of conditions and disorders, e.g., an inflammatory disorder, a neuronal disorder or other disorder described herein. When used to treat a human subject, the antibody is preferably a human, humanized or otherwise effectively human antibody.

In one aspect, the disclosure features a protein that includes a first and a second immunoglobulin variable domain sequence and that binds to TWEAK, e.g., human TWEAK. The protein can bind to TWEAK, e.g., with an affinity corresponding to a $K_D$ of less than $10^{-7}$ M, e.g., $10^{-8}$, $10^{-9}$, $10^{-10}$, $10^{-11}$ M or better. The protein is also referred to herein as an "anti-TWEAK antibody." The first and second immunoglobulin variable domain sequences can include at least a sufficient portion of an immunoglobulin variable domain to form an antigen binding site that binds to TWEAK. Typically, the first and second immunoglobulin variable domain sequences correspond to immunoglobulin variable domain sequences of a heavy and light chain, respectively, e.g., a paired or otherwise compatible heavy and light chain.

The antibody can bind to an epitope on TWEAK which includes at least one, two, three or four amino acid residues from an epitope on TWEAK recognized by P2D10, to a peptide from TWEAK that is bound by P2D10 (e.g., a peptide less than 25, 20, or 15 amino acids in length) or to a region of TWEAK recognized by P2D10. For example, the antibody specifically binds to an epitope, e.g., a linear or a conformational epitope, of TWEAK, in particular human TWEAK, e.g., the soluble region of TWEAK. The antibody may compete with P2D10 for binding to TWEAK, e.g., to human TWEAK. The antibody may competitively inhibit binding of P2D10 to TWEAK, e.g., human TWEAK. In one embodiment, the antibody may bind to an epitope which overlaps with that of P2D10, e.g., includes at least one, two, three or four amino acids in common with the P2D10 epitope, or an epitope which, when bound, sterically prevents TWEAK interaction with P2D10.

For example, the anti-TWEAK antibody can bind to TWEAK and modulate, e.g., inhibit, an interaction (e.g., binding) between TWEAK and a TWEAK receptor, e.g., Fn14 (e.g., human Fn14). The antibody may also reduce signaling activity of a TWEAK receptor. The antibody may target TWEAK, sequester TWEAK, and/or modulate the in vivo stability of TWEAK.

In one embodiment, the antibody specifically binds to at least a part of the interaction site on TWEAK that contacts Fn14 (e.g., human Fn14). The antibody may compete with Fn14 for binding to TWEAK, e.g., to human TWEAK. The antibody may competitively inhibit binding of Fn14 to TWEAK. The antibody may interact with an epitope on TWEAK which, when bound, sterically prevents interaction between TWEAK and Fn14 (e.g., between human TWEAK and human Fn14).

In one embodiment, the antibody can inhibit one or more TWEAK-associated activities with an $IC_{50}$ of about 50 nM to 5 pM, typically about 100 to 250 pM or less. For example, the antibody can inhibit the ability of TWEAK to promote endothelial cell proliferation or neovascularization. In one embodiment, the anti-TWEAK antibody reduces at least one TWEAK-associated activity, e.g., such that the antibody can modulate an inflammatory condition when administered to a subject.

In other embodiments, the antibody can associate with TWEAK with kinetics in the range of $10^3$ to $10^8$ M$^{-1}$ s$^{-1}$, typically $10^4$ to $10^7$ M$^{-1}$ s$^{-1}$. In yet another embodiment, the antibody has dissociation kinetics in the range of $10^{-2}$ to $10^{-6}$ s$^{-1}$, typically $10^{-2}$ to $10^{-5}$ s$^{-1}$. In one embodiment, the antibody binds to TWEAK, e.g., human TWEAK, with an affinity and/or kinetics similar to (e.g., within a factor of five or ten of) monoclonal antibody P2D10, or modified forms thereof, e.g., chimeric forms or humanized forms thereof (e.g., a humanized form described herein). The affinity and binding kinetics of the anti-TWEAK antibody can be tested, e.g., using biosensor technology (BIACORE™).

In one embodiment, the antibody is an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody. For example, the antibody is in a composition that includes less than 20 other species of anti-TWEAK antibodies, e.g., in a composition that does not include another species of anti-TWEAK antibody.

The antibody can be effectively human. An "effectively human" antibody is an antibody that includes a sufficient number of human amino acid positions such that the antibody does not elicit an immunogenic response in a normal human. Preferably, the protein does not evoke a neutralizing antibody response, e.g., the human anti-murine antibody (HAMA) response. HAMA can be problematic in a number of circumstances, e.g., if the antibodies are desired to be administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al. (1986) *Hybridoma*, 5:5117-5123).

For example, the antibody can be a human, humanized, CDR-grafted, chimeric, mutated, affinity matured, deimmunized, synthetic or otherwise in vitro-generated antibody, and combinations thereof. In one embodiment, the anti-TWEAK antibody is a humanized antibody.

The heavy and light chains of the anti-TWEAK antibody can be substantially full-length. The protein can include at least one, and preferably two, complete heavy chains, and at least one, and preferably two, complete light chains) or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

In one embodiment, the protein includes at least one, two and preferably three CDRs from the light or heavy chain variable region of an antibody disclosed herein, e.g., P2D10. In this context, CDRs refer to CDRs as defined by Chothia's hypervariable loops. For example, the protein includes, in the heavy chain variable domain sequence, at least one, two, or three of the following sequences within a CDR region:

GFTFSRYAMS (CDR1) (SEQ ID NO:1),
EISSGGSYPYYPDTVTG (CDR2) (SEQ ID NO:2),
VLYYDYDGDRIEVMDY (CDR3) (SEQ ID NO:3), or a CDR having an amino acid sequence that differs by no more than 4, 3, 2.5, 2, 1.5, 1, or 0.5 alterations (e.g., substitutions, insertions or deletions) for every 10 amino acids (e.g., the number of differences being proportional to the CDR length) relative to a sequence listed above, e.g., at least one alteration but not more than two, three, or four per CDR. The heavy chain variable domain sequence may include these CDR sequences particularly in CDR3, or in at least two CDRs, e.g., CDR1 and CDR3, CDR2 and CDR3, or in all three CDRs.

The protein can include, in the heavy chain variable domain sequence, at least one, two, or three of the following sequences within a CDR region (amino acids in parentheses represent alternatives for the particular position):

```
(i)    G-(YF)-(NT)-F-(STDN)-(RY)-Y-A-(MIL)-(HS);,   (SEQ ID NO:4)
or (ii)   Y-Y-(PV)-D-(TS)-V-(TK)-G;                    (SEQ ID NO:5)

(iii)  (VL)-(IL)-(YF)-(YF)-D-(YF)-D;                (SEQ ID NO:6)
or (DE)-(RK)-(ILVM)-(EQD)-(VAL)-M-(DE);.        (SEQ ID NO:7)
```

The protein can include, in the light chain variable domain sequence, at least one, two, or three of the following sequences within a CDR region:

RSSQSLVSSKGNTYLH; (CDR1) (SEQ ID NO:8),
KVSNRFS; (CDR2) (SEQ ID NO:9), and
SQSTHFPRT; (CDR3) (SEQ ID NO: 10), or a CDR having an amino acid sequence that differs by no more than 4, 3, 2.5, 2, 1.5, 1, or 0.5 alterations (e.g., substitutions, insertions or deletions) for every 10 amino acids (e.g., the number of differences being proportional to the CDR length) relative to a sequence listed above, e.g., at least one alteration but not more than two, three, or four per CDR. The light chain variable domain sequence may include these CDR sequences particularly in CDR3, or in at least two CDRs, e.g., CDR1 and CDR3, CDR2 and CDR3, or in all three CDRs.

The protein can include, in the light chain variable domain sequence, at least one, two, or three of the following sequences within a CDR region (amino acids in parentheses represent alternatives for the particular position):

```
(i)    (RK)-S-S-Q-S-(LI)-(KV)-S-S-(KR)-G-N-(TN)-Y-L-(EHDNQY);,  (SEQ ID NO: 11)
or
       (RK)-S-S-Q-S-(LI)-V-S-S-(KR)-G-N-(TN)-Y-L-H;             (SEQ ID NO: 12)

(ii)   (KE)-(LVI)-S-(NYS)-(RW)-(FAD)-S;,                        (SEQ ID NO:13)
or
       K(LVI)-S-(NYS)-R-(FAD)-S;,                               (SEQ ID NO:14)
and (iii)  (SM)-Q-(GSA)-(ST)-(HEQ)-(FWL)-P;                         (SEQ ID NO: 15)
or
       S-Q-(GSA)-(SIT)-(HEQ)-F-P;.                              (SEQ ID NO: 16)
```

In one preferred embodiment, the protein includes all six CDR's from P2D10 or closely related CDRs, e.g., CDRs which are identical or which have at least one amino acid alteration, but not more than two, three or four alterations (e.g., substitutions, deletions, or insertions), or other CDR described herein.

In still another example, the protein includes at least one, two, or three CDR regions that have the same canonical structures and the corresponding Chothia CDR regions of P2D10, e.g., the same canonical structures as at least CDR1 and/or CDR2 of the heavy and/or light chain variable domains of P2D10.

The protein can include one of the following sequences:

```
                                                    (SEQ ID NO:17)
DIVMTQTPLSLPVTPGEPASISCRSSQSLVSSKGNTYLHWYLQKPGQSP

QLLIYKVSNRFSGVPDRFSGSGSGTDFTLKISRVEAEDVGVYYCSQSTH

FPRT
```

-continued
```
                                                    (SEQ ID NO:18)
DIVMTQTPLSLPVTPGEPASISCRSSQSLVSSKGNTYLHWYLQKPGQSP

QLLIYKVSNRFSGVPDRFSGSGSGTDFTLKISRVEAEDVGVYYCSQSTH

FPRT (SEQ ID NO:19)
DVVMTQSPLSLPVTLGQPASISCRSSQSLVSSKGNTYLHWFQQRPGQSP

RRLIYKVSNRFSGVPDRFSGSGSGTDFTLKISRVEAEDVGVYYCSQSTH

FPRT (SEQ ID NO:20)
DVVMTQSPLSLPVTLGQPASISCRSSQSLVSSKGNTYLHWFQQRPGQSP

RRLIYKVSNRFSGVPDRFSGSGSGTDFTLKISRVEAEDVGVYYCSQSTH

FPRT
```

(SEQ ID NO:21)
DIVMTQTPLSLSVTPGQPASISCRSSQSLVSSKGNTYLHWYLQKPGQSP
QLLIYKVSNRFSGVPDRFSGSGSGTDFTLKISRVEAEDVGVYYCSQSTH
FPRT (SEQ ID NO:22)
DIVMTQTPLSLSVTPGQPASISCRSSQSLVSSKGNTYLHWYLQKPGQPP
QLLIYKVSNRFSGVPDRFSGSGSGTDFTLKISRVEAEDVGVYYCSQSTH
FPRT (SEQ ID NO:23)
DIVMTQSPLSLPVTPGEPASISCRSSQSLVSSKGNTYLHWYLQKPGQSP
QLLIYKVSNRFSGVPDRFSGSGSGTDFTLKISRVEAEDVGVYYCSQSTH
FPRT (SEQ ID NO:24)
DIVMTQSPLSLPVTPGEPASISCRSSQSLVSSKGNTYLHWYLQKPGQSP
QLLIYKVSNRFSGVPDRFSGSGSGTDFTLKISRVEAEDVGVYYCSQSTH
FPRT (SEQ ID NO:25)
DIVMTQTPLSSPVTLGQPASISCRSSQSLVSSKGNTYLHWLQQRPGQPP
RLLIYKVSNRFSGVPDRFSGSGAGTDFTLKISRVEAEDVGVYYCSQSTH
FPRT (SEQ ID NO:26)
DIQMTQSPSSLSASVGDRVTITCRSSQSLVSSKGNTYLHWYQQKPGKAP
KLLIYKVSNRFSGVPSRFSGSGSGTDFTLTISSLQPEDFATYYCSQSTH
FPRT or a sequence that has fewer than eight, seven, six, five, four, three, or two alterations (e.g., substitutions, insertions or deletions, e.g., conservative substitutions or a substitution for an amino acid residue at a corresponding position in P2D10, huP2D10-L1, or huP2D10-L2). Exemplary substitutions are at one of the following Kabat positions: 2, 4, 6, 35, 36, 38, 44, 47, 49, 62, 64-69, 85, 87, 98, 99, 101, and 102. The substitutions can, for example, substitute one or more amino acids from P2D10 into corresponding positions in a framework region, e.g., a human framework region, e.g., in FR2 (e.g., at position 46 to Phe according to consecutive numbering) and in FR3 (e.g., at position 87 to Phe).

The protein can include one of the following sequences in the heavy chain variable domain:

(SEQ ID NO:27)
QVQLVQSGAEVKKPGASVKVSCKASGFTFSRYANSWVRQAPGQGLEWMG
EISSGGSYPYYPDTVTGRVTMTRDTSISTAYMELSRLRSDDTAVYYCAR
VLYYDYDGDRIE (SEQ ID NO:28)
QVQLVQSGAEVKKPGASVKVSCKASGFTFSRYAMSWVRQAPGQRLEWMG
EISSGGSYPYYPDTVTGRVTITRDTSASTAYMELSSLRSEDTAVYYCAR
VLYYDYDGDRIE (SEQ ID NO:29)
QVQLVQSGAEVKKPGASVKVSCKASGFTFSRYAMSWVRQATGQGLEWMG
EISSGGSYPYYPDTVTGRVTMTRNTSISTAYMELSSLRSEDTAVYYCAR
VLYYDYDGDRIE (SEQ ID NO:30)
QVQLVQSGAEVKKPGASVKVSCKASGFTFSRYAMSWVRQAPGQGLEWMG
EISSGGSYPYYPDTVTGRVTMTTDTSTSTAYMELRSLRSDDTAVYYCAR
VLYYDYDGDRIE (SEQ ID NO:31)
QVQLVQSGAEVKKPGASVKVSCKVSGFTFSRYAMSWVRQAPGKGLEWMG
EISSGGSYPYYPDTVTGRVTMTEDTSTDTAYMELSSLRSEDTAVYYCAT
VLYYDYDGDRIE (SEQ ID NO:32)
QMQLVQSGAEVKKTGSSVKVSCKASGFTFSRYAMSWVRQAPGQALEWMG
EISSGGSYPYYPDTVTGRVTITRDRSMSTAYMELSSLRSEDTAMYYCAR
VLYYDYDGDRIE (SEQ ID NO:33)
QVQLVQSGAEVKKPGASVKVSCKASGFTFSRYAMSWVRQAPGQGLEWMG
EISSGGSYPYYPDTVTGRVTMTRDTSTSTVYMELSSLRSEDTAVYYCAR
VLYYDYDGDRIE (SEQ ID NO:34)
QMQLVQSGPEVKKPGTSVKVSCKASGFTFSRYAMSWVRQARGQRLEWIG
EISSGGSYPYYPDTVTGRVTITRDMSTSTAYMELSSLRSEDTAVYYCAA
VLYYDYDGDRIE (SEQ ID NO:35)
EVQLVESGGGLVQPGGSLRLSCAASGFTFSRYAMSWVRQAPGKGLEWVA
EISSGGSYPYYPDTVTGRFTISRDNAKNSLYLQMNSLRAEDTAVYYCAR
VLYYDYDGDRIE (SEQ ID NO:36)
EVQLVESGGGLVQPGRSLRLSCAASGFTFSRYAMSWVRQAPGKGLEWVS
EISSGGSYPYYPDTVTGRFTISRDNAKNSLYLQMNSLRAEDTALYYCAK
DVLYYDYDGDRIE (SEQ ID NO:37)
QVQLVESGGGLVKPGGSLRLSCAASGFTFSRYAMSWIRQAPGKGLEWVS
EISSGGSYPYYPDTVTGRFTISRDNAKNSLYLQMNSLRAEDTAVYYCAR
VLYYDYDGDRIE (SEQ ID NO:38)
EVQLVESGGGLVKPGGSLRLSCAASGFTFSRYAMSWVRQAPGKGLEWVG
EISSGGSYPYYPDTVTGRFTISRDDSKNTLYLQMNSLKTEDTAVYYCTT
VLYYDYDGDRIE (SEQ ID NO:39)
EVQLVESGGGVVRPGGSLRLSCAASGFTFSRYAMSWVRQAPGKGLEWVS
EISSGGSYPYYPDTVTGRFTISRDNAKNSLYLQMNSLRAEDTALYHCAR
VLYYDYDGDRIE (SEQ ID NO:40)
EVQLVESGGGLVKPGGSLRLSCAASGFTFSRYAMSWVRQAPGKGLEWVS
EISSGGSYPYYPDTVTGRFTISRDNAKNSLYLQMNSLRAEDTAVYYCAR
VLYYDYDGDRIE

```
                                            (SEQ ID NO:41)
EVQLLESGGGLVQPGGSLRLSCAASGFTFSRYAMSWVRQAPGKGLEWVS

EISSGGSYPYYPDTVTGRFTISRDNSKNTLYLQMNSLRAEDTAVYYCAK

VLYYDYDGDRIE
                                            (SEQ ID NO:42)
QVQLVESGGGVVQPGRSLRLSCAASGFTFSRYAMSWVRQAPGKGLEWVA

EISSGGSYPYYPDTVTGRFTISRDNSKNTLYLQMNSLRAEDTAVYYCAK

VLYYDYDGDRIE
                                            (SEQ ID NO:43)
QVQLVESGGGVVQPGRSLRLSCAASGFTFSRYAMSWVRQAPGKGLEWVA

EISSGGSYPYYPDTVTGRFTISRDNSKNTLYLQMNSLRAEDTAVYYCAR

VLYYDYDGDRIE
                                            (SEQ ID NO:44)
QVQLVESGGGVVQPGRSLRLSCAASGFTFSRYAMSWVRQAPGKGLEWVA

EISSGGSYPYYPDTVTGRFTISRDNSKNTLYLQMNSLRAEDTAVYYCAK

VLYYDYDGDRIE
                                            (SEQ ID NO:45)
QVQLVESGGGVVQPGRSLRLSCAASGFTFSRYAMSWVRQAPGKGLEWVA

EISSGGSYPYYPDTVTGRFTISRDNSKNTLYLQMNSLRAEDTAVYYCAR

VLYYDYDGDRIE
                                            (SEQ ID NO:46)
EVQLVESGGVVVQPGGSLRLSCAASGFTFSRYAMSWVRQAPGKGLEWVS

EISSGGSYPYYPDTVTGRFTISRDNSKNSLYLQMNSLRTEDTALYYCAK

DVLYYDYDGDRIE
                                            (SEQ ID NO:47)
EVQLVESGGGLVQPGGSLRLSCAASGFTFSRYAMSWVRQAPGKGLEWVS

EISSGGSYPYYPDTVTGRFTISRDNAKNSLYLQMNSLRDEDTAVYYCAR

VLYYDYDGDRIE
                                            (SEQ ID NO:48)
EVQLVESGGGLVQPGRSLRLSCTASGFTFSRYAMSWFRQAPGKGLEWVG

EISSGGSYPYYPDTVTGRFTISRDGSKSIAYLQMNSLKTEDTAVYYCTR

VLYYDYDGDRIE
                                            (SEQ ID NO:49)
EVQLVESGGGLVQPGGSLRLSCAASGFTFSRYAMSWVRQAPGKGLEYVS

EISSGGSYPYYPDTVTGRFTISRDNSKNTLYLQMGSLRAEDMAVYYCAR

VLYYDYDGDRIE
``` or a sequence that has fewer than eight, seven, six, five, four, three, or two alterations (e.g., substitutions, insertions or deletions, e.g., conservative substitutions or a substitution for an amino acid residue at a corresponding position in P2D10). Exemplary substitutions are at one of the following Kabat positions: 2, 4, 6, 25, 36, 37, 39, 47, 48, 93, 94, 103, 104, 106, and 107. The substitutions can, for example, substitute one or more amino acids from P2D10 into corresponding positions in a framework region, e.g., a human framework region.

In one embodiment, the heavy chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or more identical to the heavy chain framework of one of the following germline V segment sequences: DP-25, DP-1, DP-12, DP-9, DP-7, DP-31, DP-32, DP-33, DP-58, DP-54, other VH I subgroup germline sequence, other VH III subgroup germline sequence, or another V gene which is compatible with the canonical structure class 1-3 (see, e.g., Chothia et al. (1992) *J. Mol. Biol.* 227:799-817; Tomlinson et al. (1992) *J. Mol. Biol.* 227:776-798). Other frameworks compatible with the canonical structure class 1-3 include frameworks with the one or more of the following residues according to Kabat numbering: Ala, Gly, Thr, or Val at position 26; Gly at position 26; Tyr, Phe, or Gly at position 27; Phe, Val, Ile, or Leu at position 29; Met, Ile, Leu, Val, Thr, Trp, or Ile at position 34; Arg, Thr, Ala, Lys at position 94; Gly, Ser, Asn, or Asp at position 54; and Arg at position 71.

In one embodiment, the light chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or more identical to the light chain framework of a Vκ II subgroup germline sequence or one of the following germline V segment sequences: A17, A1, A18, A2, A19/A3, A23, a Vκ I subgroup germline sequence (e.g., a DPK9 sequence), or another V gene which is compatible with the canonical structure class 4-1 (see, e.g., Tomlinson et al. (1995) *EMBO J.* 14:4628). Other frameworks compatible with the canonical structure class 4-1 include frameworks with the one or more of the following residues according to Kabat numbering: Val or Leu or Ile at position 2; Ser or Pro at position 25; Ile or Leu at position 27b; Gly at position 29; Phe or Leu at position 33; and Phe at position 71. Further, according to the Kabat numbering, position 48 can be Ile or Val.

In another embodiment, the light chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or more identical to the light chain framework of a Vκ I subgroup germline sequence, e.g., a DPK9 sequence.

In one embodiment, the light or the heavy chain variable framework (e.g., the region encompassing at least FR1, FR2, FR3, and optionally FR4) can be chosen from: (a) a light or heavy chain variable framework including at least 80%, 90%, 95%, or preferably 100% of the amino acid residues from a human light or heavy chain variable framework, e.g., a light or heavy chain variable framework residue from a human mature antibody, a human germline sequence, a human consensus sequence, or a human antibody described herein; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the heavy chain variable domain sequence includes human residues or human consensus sequence residues at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering).

In one embodiment, the protein includes at least one non-human CDR, e.g., a murine CDR, e.g., a CDR from P2D10, or a mutant thereof, and at least one framework which differs from a framework of P2D10 by at least one amino acid, e.g., at least 5, 8, 10, 12, 15, or 18 amino acids. For example, the proteins include one, two, three, four, five, or six such non-human CDR's and includes at least one amino acid difference in at least three of HC FR1, HC FR2, HC FR3, LC FR1, LC FR2, and LC FR3.

In one embodiment, the heavy or light chain variable domain sequence of the protein includes an amino acid sequence, which is at least 80%, 85%, 90%, 95%, 97%, 98%, 99% or more identical to a variable domain sequence of an antibody described herein, e.g., P2D10, huP2D10-1, or huP2D10-2; or which differs at least 1 or 5 residues, but less than 40, 30, 20, or 10 residues, from a variable domain sequence of an antibody described herein, e.g., P2D10, huP2D10-1, or huP2D10-2.

In one embodiment, one or both of the variable domains include amino acid positions in the framework region that are variously derived from both a murine antibody (e.g., P2D10) and a humanized antibody (e.g., 56-84m and K107) or germline sequence. For example, the variable domain will include a number of positions at which the amino acid is identical to both the murine antibody and the human antibody (or germline sequence) because the two are identical at that position. Of the remaining framework positions where the murine and human differ, at least 50, 60, 70, 80, or 90% of the positions of the variable domain are preferably identical to the human antibody (or germline sequence) rather than the murine. None, or at least one, two, three, or four of such remaining framework positions may be identical to the murine antibody rather than to the human antibody. For example, in HC FR1, one or two such positions can be murine; in HC FR2, one or two such positions can be murine; in FR3, one, two, three, or four such positions can be murine; in LC FR1, one, two, three, or four such positions can be murine; in LC FR2, one or two such positions can be murine; in LC FR3, one or two such positions can be murine.

In one embodiment, the heavy or light chain variable domain sequence of the protein includes an amino acid sequence encoded by a nucleic acid sequence described herein or a nucleic acid that hybridizes to a nucleic acid sequence described herein (e.g., a specific nucleic acid sequence or a nucleic acid sequence that encodes an amino acid sequence described herein) or its complement, e.g., under low stringency, medium stringency, high stringency, or very high stringency conditions.

The anti-TWEAK antibody can be derivatized or linked to another functional molecule, e.g., another peptide, protein, or compound. For example, the antibody can be functionally linked (e.g., by chemical coupling, genetic fusion, non-covalent association or otherwise) to one or more other molecular entities, such as another antibody (e.g., a bispecific or a multispecific antibody), toxins, radioisotopes, polymers, cytotoxic or cytostatic agents, among others.

In another aspect, the disclosure provides compositions, e.g., pharmaceutical compositions, that include a pharmaceutically acceptable carrier and an anti-TWEAK antibody, e.g., an anti-Tweak antibody described herein.

In yet another embodiment, the anti-TWEAK antibody (e.g., a pharmaceutical composition thereof) is administered to a subject who needs an anti-TWEAK antibody therapy or whose condition would be ameliorated by the antibody. For example, the anti-TWEAK antibody can be administered to a subject who has or is at risk for an inflammatory disorder, immune disorder, autoimmune disorder, neuronal disorder, a neoplastic disorder, or other disorder described herein. In one embodiment, an anti-TWEAK antibody described herein is used for the preparation of a medicament for the treatment of an inflammatory disorder, immune disorder, autoimmune disorder, neuronal disorder, a neoplastic disorder, or other disorder described herein.

In another aspect, the disclosure features a method of treating a TWEAK-associated disorder, in a subject. The method includes: administering to the subject an anti-TWEAK antibody, in an amount sufficient to treat (e.g., improve or prevent) the TWEAK-associated disorder. The anti-TWEAK antibody can be administered to the subject, alone or in combination with other therapeutic modalities as described herein. In one embodiment, the subject is a mammal, e.g., a human, e.g., a human having a TWEAK-associated disorder, e.g., a disorder disclosed herein. The antibody can be used to ameliorate one or more symptoms of such disorders. The term "treating" refers to administering a therapy in an amount, manner, and/or mode effective to improve or prevent a condition, symptom, or parameter associated with a disorder (e.g., a disorder described herein) or to prevent onset, progression, or exacerbation of the disorder, to either a statistically significant degree or to a degree detectable to one skilled in the art. Accordingly, treating can achieve therapeutic and/or prophylactic benefits. An effective amount, manner, or mode can vary depending on the subject and may be tailored to the subject. In one embodiment, an anti-TWEAK antibody described herein is used for the preparation of a medicament for the treatment of a TWEAK-associated disorder.

In another aspect, the disclosure features a method of modulating interaction between TWEAK and a TWEAK receptor protein. For example, an anti-TWEAK antibody can be used to reduce or inhibit binding, between TWEAK and a TWEAK receptor, such as Fn14. The method comprises contacting TWEAK or a complex that contains TWEAK with the antibody. The method can be used on cells in vitro e.g., in culture, e.g. in vitro or ex vivo. For example, TWEAK receptor-expressing cells can be cultured in vitro in culture medium and the contacting step can be effected by adding an anti-TWEAK antibody to the culture medium. Alternatively, the method can be performed on cells present in a subject, e.g., as part of an in vivo (e.g., therapeutic or prophylactic) protocol. For example, the anti-TWEAK antibody can be delivered locally or systemically. In one embodiment, an anti-TWEAK antibody described herein is used for the preparation of a medicament for of modulating interaction between TWEAK and a TWEAK receptor protein.

The method can include contacting TWEAK with the TWEAK receptor complex, or subunit thereof, under conditions that allow an interaction between TWEAK and the TWEAK receptor complex, or subunit thereof, to occur to thereby form a TWEAK/TWEAK receptor mixture. Generally, the anti-TWEAK antibody is provided in an effective amount, e.g., so that contacting the TWEAK/TWEAK receptor mixture with the anti-TWEAK antibody modulates, e.g., interferes with (e.g., inhibits, blocks or otherwise reduces) the interaction between TWEAK and the receptor protein or at least one function of TWEAK, e.g., TWEAK mediated signaling.

The disclosure also features nucleic acids comprising nucleotide sequences, which encode heavy and light chain variable regions of the anti-TWEAK antibodies, e.g., as described herein. For example, the disclosure features a first and second nucleic acid encoding heavy and light chain variable regions, respectively, of P2D10. In another aspect, the disclosure features host cells and vectors containing the nucleic acids described herein.

The disclosure also features the epitope of TWEAK, e.g., human TWEAK, recognized by P2D10 and proteins able to interact with the epitope. For example, proteins and peptides that include the epitope can be used to generate or screen for other binding compounds that interact with the epitope, e.g., proteins such as antibodies or small molecules. For example, a peptide that includes the epitope can be used as an immunogen or as a target for screening an expression library. It is also possible to evaluate compounds for their ability to interact with the peptide, or, by mapping or structure determination, to evaluate compounds for their ability to interact with the epitope, e.g., in the context of a mature TWEAK. An exemplary evaluation includes determining if the compound can interact with TWEAK in the presence of a competing P2D10 antibody.

Methods for delivering or targeting an agent, e.g., a therapeutic (including a genetic agent) or a cytotoxic agent, with an anti-TWEAK antibody (e.g., P2D10 or other antibody described herein) to a TWEAK-expressing cell or structure in vivo are also disclosed.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$ fragments, Fd fragments, Fv fragments, and dAb fragments) as well as full length antibodies, e.g., full length, immunoglobulins of types IgA, IgG (e.g., IgG1, IgG2, IgG3, IgG4), IgE, IgD, IgM (as well as subtypes thereof). The term "full length antibody" refers to an antibody having at least 96% of the length of a natural antibody that is processed to remove any signal sequences. A full length antibody can include the complete length of the natural antibody, e.g., residues from the amino-terminal residue of a natural antibody (e.g., a IgG1, IgG2, IgG3, IgG4) to its carboxy-terminal residue.

An "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two or more N- or C-terminal amino acids, or may include other alterations that are compatible with formation of the protein structure.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interest is at least 5, 10, 25, 50, 75, 80, 90, 95, 98, or 99% pure on a weight-weight basis.

An "epitope" refers to the site on a target compound that is bound by an antibody. In the case where the target compound is a protein, for example, an epitope may refer to the amino acids (particularly amino acid side chains) that are bound by the antibody. Overlapping epitopes include at least one common amino acid residue, e.g., at least 2, 3, 4 or 5 common amino acid residues.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. High stringency conditions (3) are the preferred conditions and the ones that should be used unless otherwise specified.

A "TWEAK-associated disorder" is any disorder in which TWEAK contributes to etiology or a disorder whose condition, symptoms, or risk of onset is altered by provision of a TWEAK blocking agent.

Unless otherwise defined, all technical and scientific terms used herein have the same meaning as commonly understood by one of ordinary skill in the art to which this invention belongs. Although methods and materials similar or equivalent to those described herein can be used in the practice or testing described herein, suitable methods and materials are described below. In addition, embodiments of the invention described with respect to Chothia CDRs may also be implemented using Kabat CDRs.

All publications, patent applications, patents, and other references mentioned herein are incorporated by reference in their entirety. In the case of conflict, the present specification, including definitions, controls. In addition, the materials, methods, and examples are illustrative only and not intended to be limiting.

DETAILED DESCRIPTION

P2D10 is an exemplary murine antibody that specifically binds to human TWEAK and inhibits TWEAK function. Variants of the P2D10 antibody are also disclosed, including exemplary humanized variants. These antibodies, other anti-TWEAK antibodies, and other TWEAK blocking agents can be used to treat or prevent TWEAK-mediated disorders, e.g., inflammatory disorders and other disorders disclosed herein.

Anti-TWEAK Antibodies

This disclosure includes the sequences of specific examples of anti-TWEAK antibodies, such as P2D10, huP2D10-1, and huP2D10-2. Particular antibodies, such as these, can be made, for example, by preparing and expressing synthetic genes that encode the recited amino acid sequences or by mutating human germline genes to provide a gene that encodes the recited amino acid sequences. Moreover, these antibodies and other anti-TWEAK antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) *Science* 228: 1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667,988; and 5,885,793.

In addition to the use of display libraries, other methods can be used to obtain a TWEAK-binding antibody. For example, the TWEAK protein or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR-grafting method that may be used to prepare humanized antibodies described herein (U.S. Pat. No. 5,225,539). All or some of the CDRs of a particular human antibody may be replaced with at least a portion of a non-human antibody. It may only be necessary to replace the CDRs required for binding or binding determinants of such CDRs to arrive at a useful humanized antibody that binds to TWEAK.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) *Science* 229:1202-1207, by Oi et al. (1986) *BioTechniques* 4:214, and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Bio.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

A non-human TWEAK-binding antibody may also be modified by specific deletion of human T cell epitopes or "deimmunization" by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and $V_L$ can be constructed by mutagenesis or other synthetic methods (e.g., de novo synthesis, cassette replacement, and so forth). A mutagenized variable sequence can, optionally, be fused to a human constant region, e.g., human IgG1 or kappa constant regions.

In some cases, a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs can be eliminated by substitutions outside the CDRs. In some cases, an alteration within a CDR is the only option, and thus variants with and without this substitution can be tested. In other cases, the substitution required to remove a potential T cell epitope is at a residue position within the framework that might be critical for antibody binding. In these cases, variants with and without this substitution are tested. Thus, in some cases several variant deimmunized heavy and light chain variable regions are designed and various heavy/light chain combinations are tested to identify the optimal deimmunized antibody. The choice of the final deimmunized antibody can then be made by considering the binding affinity of the different variants in conjunction with the extent of deimmunization, particularly, the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; 5,530,101; and 6,407,213; Tempest et al. (1991) *Biotechnology* 9:266-271. Still another method is termed "humaneering" and is described, for example, in U.S. 2005-008625.

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08). See also, e.g., U.S. 2005-0037000.

Affinity Maturation. In one embodiment, an anti-TWEAK antibody is modified, e.g., by mutagenesis, to provide a pool of modified antibodies. The modified antibodies are then evaluated to identify one or more antibodies which have altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.* 22:259-306. Removal of any carbohydrate moieties present on the antibodies may be accomplished chemically or enzymatically as described in the art (Hakimuddin et al. (1987) *Arch. Biochem. Biophys.* 259:52; Edge et al. (1981) *Anal. Biochem.* 118:131; and Thotakura et al. (1987) *Meth. Enzymol.* 138: 350). See, e.g., U.S. Pat. No. 5,869,046 for a modification that increases in vivo half life by providing a salvage receptor binding epitope.

In one embodiment, an antibody has CDR sequences that differ only insubstantially from those of P2D10. Insubstantial differences include minor amino acid changes, such as substitutions of 1 or 2 out of any of typically 5-7 amino acids in the sequence of a CDR, e.g., a Chothia or Kabat CDR. Typically an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) *J. Immun.* 147:2657-62; Morgan et al. (1995) *Immunology* 86:319-24), or changing the species from which the constant region is derived.

The anti-TWEAK antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) *Protein Eng.* 9(6): 531-7.

Antibody Production. Some antibodies, e.g., Fab's, can be produced in bacterial cells, e.g., *E. coli* cells. Antibodies can also be produced in eukaryotic cells. In one embodiment, the antibodies (e.g., scFv's) are expressed in a yeast cell such as *Pichia* (see, e.g., Powers et al. (2001) *J Immunol Methods.* 251:123-35), *Hanseula*, or *Saccharomyces*.

In one preferred embodiment, antibodies are produced in mammalian cells. Exemplary mammalian host cells for expressing an antibody include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced.

In an exemplary system for antibody expression, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) *Adv. Immunol.* 51:1-84; Jefferis et al. (1998) *Immunol. Rev.* 163:59-76). In one embodiment, the Fc domain is produced in a mammalian expression system that appropriately glycosylates the residue corresponding to asparagine 297. The Fc domain or other region of the antibody can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Characterization

The binding properties of an antibody may be measured by any standard method, e.g., one of the following methods: BIACORE™ analysis, Enzyme Linked Immunosorbent Assay (ELISA), Fluorescence Resonance Energy Transfer (FRET), x-ray crystallography, sequence analysis and scanning mutagenesis. The ability of a protein to inhibit one or more activities of TWEAK can be evaluated in vitro or in an animal model of a disorder, e.g., a disorder described herein. Preferably, the antibody has a statistically significant effect that indicates that the antibody inhibits one or more activities of TWEAK.

In one embodiment, an antibody is evaluated for inhibition of the ability of TWEAK to stimulate production of IL-8, MMP-1, PGE2, IL-6, IP-10 and RANTES in dermal fibroblasts. See Chicheportiche et al. (2002) *Arthritis Res.* 4(2): 126-133 for suitable assay conditions.

In another embodiment, an antibody is evaluated for its ability to inhibit TWEAK from stimulating the proliferation of an endothelial cell. See, e.g., U.S. 2003-0211993 which describes a proliferation assay (as well as other useful assays) as follows: HVEC are plated in 96-well microtiter plates at subconfluence (4000 cells per well) and cultured overnight in CS-C Medium without addition of supplier growth supplements. Media is replaced with complete Media, or with basal media. Cells are cultured in basal media with or without TWEAK (100 ng/ml), bFGF using a 1/500 to 1/1000 dilution of bFGF growth supplement (Clonetics) or 1 ng/ml (R&D Systems), VEGF (10 ng/ml) or combinations of these factors. Where indicated, 10 Hg/ml of the antibody being tested or a control antibody is also added. Cells are incubated at 37° C. with 5% $CO_2$ for three days and proliferation was measured by pulsing with $^3$H-Thymidine for the last 10 hours of culture. Cell-bound radioactivity can be measured with a BETAPLATE™ (EG&G Wallac, Gaithersburg, Md.). A decrease in proliferation mediated by TWEAK or the combination of TWEAK and bFGF can indicate that the antibody is effective at blocking TWEAK activity.

Surface Plasmon Resonance (SPR). The binding interaction of a protein of interest and a target (e.g., TWEAK) can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $K_{on}$ and $K_{off}$, for the binding of a biomolecule to a target.

Epitopes can also be directly mapped by assessing the ability of different antibodies to compete with each other for binding to TWEAK (e.g., human TWEAK, particularly soluble human TWEAK) using BIAcore chromatographic techniques (Pharmacia BIAtechnology Handbook, "Epitope Mapping", Section 6.3.2, (May 1994); see also Johne et al. (1993) *J. Immunol. Methods,* 160:191-198). Additional general guidance for evaluating antibodies, e.g., in Western blots and immunoprecipitation assays, can be found in *Antibodies: A Laboratory Manual*, ed. by Harlow and Lane, Cold Spring Harbor press (1988)).

TWEAK-Associated Disorders

An anti-TWEAK antibody (such as an antibody described herein) can be used to treat a variety of disorders, such as a TWEAK-associated disorder. For example, the antibody can be used to treat inflammatory, immune, or autoimmune disorders in patients, as well as neoplastic disorders. Examples of inflammatory TWEAK-associated disorders include rheumatoid arthritis, psoriatic arthritis, ankylosing spondylitis, inflammatory bowel disease (including ulcerative colitis and Crohn's disease), psoriasis, or inflammatory myositis. Still other examples of inflammatory disorders that can be treated include Langerhans-cell histiocytosis, adult respiratory distress syndrome/bronchiolitis obliterans, Wegener's granulomatosis, vasculitis, cachexia, stomatitis, idiopathic pulmonary fibrosis, dermatomyositis or polymyositis, non-infectious scleritis, chronic sarcoidosis with pulmonary involvement, myelodysplastic syndromes/refractory anemia with excess blasts, ulcerative colitis, moderate to severe chronic obstructive pulmonary disease, and giant cell arteritis.

A subject who is at risk for, diagnosed with, or who has one of these disorders can be administered an anti-TWEAK antibody in an amount and for a time to provide an overall therapeutic effect. The anti-TWEAK antibody can be administered alone or in combination with other agents. For example, U.S. Ser. No. 60/679,518 describes methods for administering a TWEAK blocking agent in combination with a TNF-α blocking agent. In the case of a combination therapy, the amounts and times of administration can be those that provide, e.g., a synergistic therapeutic effect. Further, the administration of the TWEAK blocking agent (with or without the second agent) can be used as a primary, e.g., first line treatment, or as a secondary treatment, e.g., for subjects who have an inadequate response to an previously administered therapy (i.e., a therapy other than one with a TWEAK blocking agent).

Rheumatoid Arthritis (RA)

An anti-TWEAK antibody (such as an antibody described herein) can be used to treat rheumatoid arthritis and related disorders. Rheumatoid arthritis ("RA") is a chronic inflammatory disease that causes pain, swelling, stiffness, and loss of function, primarily in joints. RA frequently begins in the synovium, the membrane that surrounds a joint creating a protective sac. In many individuals suffering from RA, leukocytes infiltrate from the circulation into the synovium causing continuous abnormal inflammation (e.g., synovitis). Consequently, the synovium becomes inflamed, causing warmth, redness, swelling, and pain. The collagen in the cartilage is gradually destroyed, narrowing the joint space and eventually damaging bone. The inflammation causes erosive bone damage in the affected area. During this process, the cells of the synovium grow and divide abnormally, making the normally thin synovium thick and resulting in a joint that is swollen and puffy to the touch.

As RA progresses, abnormal synovial cells can invade and destroy the cartilage and bone within the joint. The surrounding muscles, ligaments, and tendons that support and stabilize the joint can become weak and unable to work normally. RA also may cause more generalized bone loss that may lead to osteoporosis, making bones fragile and more prone to fracture. All of these effects cause the pain, impairment and deformities associated with RA. Regions that can be effected include the wrists, knuckles, knees and the ball of the foot. Often, many joints may be involved, and even the spine can be affected. In about 25% of people with RA, inflammation of small blood vessels can cause rheumatoid nodules, or lumps, under the skin, that often form close to the joints. As the disease progresses, fluid may also accumulate, particularly in the ankles. Many patients with RA also develop anemia, or a decrease in the normal number of red blood cells.

RA encompasses a number of disease subtypes, such as Felty's syndrome, seronegative RA, "classical" RA, progressive and/or relapsing RA, and RA with vasculitis. Some experts classify the disease into type 1 or type 2. Type 1, the less common form, lasts a few months at most and leaves no permanent disability. Type 2 is chronic and lasts for years, sometimes for life. RA can also manifest as subcutaneous rheumatoid nodules, visceral nodules, vasculitis causing leg ulcers or mononeuritis multiplex, pleural or pericardial effusions, lymphadenopathy, Felty's syndrome, Sjogren's syndrome, and episcleritis. These disease subtypes and also subjects showing one or more of the above symptoms can be treated using the antibodies described herein.

RA can be assessed by a variety of clinical measures. Some exemplary indicia include the total Sharp score (TSS), Sharp erosion score, and the HAQ disability index. The methods herein can be used to achieve an improvement for at least one of these indicia. The therapeutic properties of an anti-TWEAK antibody for treating RA can be evaluated in an animal model, e.g., using the mouse collagen-induced arthritis (mCIA) model (see e.g., Stuart et al., *J. Clin. Invest.* 69:673-683 (1982).

Multiple Sclerosis

An anti-TWEAK antibody (such as an antibody described herein) can be used to treat multiple sclerosis (MS) and related disorders. MS is a central nervous system disease that is characterized by inflammation and loss of myelin sheaths.

Patients having MS may be identified by criteria establishing a diagnosis of clinically definite MS as defined by the workshop on the diagnosis of MS (Poser et al., *Ann. Neurol.* (1983) 13:227). Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid.

Effective treatment of multiple sclerosis may be examined in several different ways. The following parameters can be used to gauge effectiveness of treatment. Three main criteria are used: EDSS (extended disability status scale), appearance of exacerbations or MRI (magnetic resonance imaging). The EDSS is a means to grade clinical impairment due to MS (Kurtzke (1983) *Neurology* 33:1444). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of in EDSS indicates an effective treatment (Kurtzke (1994) *Ann. Neurol.* 36:573-79).

An exemplary animal model for multiple sclerosis is the experimental autoimmune encephalitis (EAE) mouse model, e.g., as described in Tuohy et al. (*J. Immunol.* (1988) 141: 1126-1130), Sobel et al. (*J. Immunol.* (1984) 132: 2393-2401), and Traugott (*Cell Immunol.* (1989) 119: 114-129). Mice can be administered an antibody described herein prior to EAE induction. The mice are evaluated for characteristic criteria to determine the efficacy of the antibody.

Stroke

An anti-TWEAK antibody (such as an antibody described herein) can be used to treat a subject who has experienced a stroke, e.g., a thromboembolic or hemorrhagic stroke (e.g., within the last 48, 24, 12, 8, or 2 hours), or to prevent a stroke, e.g., in a subject at risk for stroke. Exemplary methods are described in U.S. Ser. No. 60/653,811. Stroke is a general term for acute brain damage resulting from disease of blood vessels. Stroke can be classified into at least two main categories: hemorrhagic stroke (resulting from leakage of blood outside of the normal blood vessels) and ischemic stroke (cerebral ischemia due to lack of blood supply). Some events that can cause ischemic stroke include thrombosis, embolism, and systemic hypoperfusion (with resultant ischemia and hypoxia).

Stroke generally causes neuronal death and injury in the brain by oxygen deprivation and secondary events. The area of the brain that dies as a result of the lack of blood supply or other damage is called an infarct. In some cases, the treatments described herein can be used to reduce or minimize the size of an infarct, e.g., by reducing secondary events that cause neuronal death or injury.

Obstruction of a cerebral artery resulting from a thrombus which has built up on the wall of a brain artery is generally called cerebral thrombosis. In cerebral embolism, the occlusive material blocking the cerebral artery arises downstream in the circulation (e.g. an embolus is carried to the cerebral artery from the heart). Because it is difficult to discern whether a stroke is caused by thrombosis or embolism, the term thromboembolism is used to cover both these types of stroke. Systemic hypoperfusion may arise as a consequence of decreased blood levels, reduced hematocrit, low blood pressure or inability of the heart to pump blood adequately.

Further, an anti-TWEAK antibody can be administered as a prophylactic stroke therapy, or as a component thereof, e.g., to a subject who has experienced a transient ischemic attack (TIA) or is exhibiting symptoms of TIA.

Neuronal Disorders

An anti-TWEAK antibody (such as an antibody described herein) can be used to treat or prevent neuronal disorders such as mechanical neuronal traumas and neurodegenerative disorders. Examples of mechanical neuronal traumas include spinal cord injury (SCI) and traumatic brain injury (TBI). Examples of neurodegenerative disorders include amyotrophic lateral sclerosis (ALS), progressive bulbar palsy (PBP), primary lateral sclerosis (PLS), progressive muscular atrophy (PMA), Parkinson's Disease, Huntington's Disease (HD), and Alzheimer's Disease. See, e.g., U.S. Ser. No. 60/653,813. In one embodiment, the neuronal disorder is primarily characterized by destruction or death of nerve cells, e.g., of motor neurons (e.g., ALS), of striatal neurons of basal ganglia and/or cortical neurons (e.g., Huntington's disease), of substantia nigra neurons (e.g., Parkinson's disease).

Cancer

TWEAK and its receptors may be involved in the development of at least some types of cancer, e.g., a pancreatic cancer. An anti-TWEAK antibody (such as an antibody described herein) can be used to treat or prevent cancers (e.g., adenocarcinomas) and other neoplastic disorders. See, e.g., "TREATMENT OF CANCER," U.S. Ser. No. 60/685,465, filed on May 27, 2005.

Pharmaceutical Compositions

An anti-TWEAK antibody (such as an antibody described herein) can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) *J. Pharm. Sci.* 66:1-19).

Pharmaceutical formulation is a well-established art, and is further described, e.g., in Gennaro (ed.), *Remington. The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients American Pharmaceutical Association*, 3$^{rd}$ ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, the anti-TWEAK antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the anti-TWEAK antibody may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York (1978).

An anti-TWEAK antibody can be modified, e.g., with a moiety that improves its stabilization and/or retention in circulation, e.g., in blood, serum, or other tissues, e.g., by at least 1.5, 2, 5, 10, or 50 fold. The modified antibody can be evaluated to assess whether it can reach sites of inflammation, e.g., joints.

For example, the anti-TWEAK antibody can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, the anti-TWEAK antibody can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

In some implementations, the anti-TWEAK antibody can also be coupled to or otherwise associated with a label or other agent, e.g., another therapeutic agent such as a cytotoxic or cytostatic agent, although, in many embodiments, this configuration is unnecessary. Examples of cytotoxic and chemotherapeutic agents include taxol, cytochalasin B, gramicidin D, vinblastine, doxorubicin, daunorubicin, a maytansinoid (e.g., maytansinol or the DM1 maytansinoid, a sulfhydryl-containing derivative of maytansine), mitoxantrone, mithramycin, actinomycin D, 1-dehydrotestosterone, glucocorticoids, procaine, taxane, tetracaine, lidocaine, propranolol, and puromycin and analogs or homologs thereof.

When the anti-TWEAK antibody is used in combination with a second agent (e.g., an anti-TNF-α antibody or other agent), the two agents can be formulated separately or together. The agents can be formulated or otherwise used in a synergistically effective amount. It is also possible to use one or both of the agents in amounts less than would be used for mono-therapy. For example, the respective pharmaceutical compositions can be mixed, e.g., just prior to administration, and administered together or can be administered separately, e.g., at the same or different times.

It is also possible to use other TWEAK blocking agents, e.g., agents described in U.S. Ser. No. 60/679,518. The agent may be any type of compound (e.g., small organic or inorganic molecule, nucleic acid, protein, or peptide mimetic) that can be administered to a subject. In one embodiment, the blocking agent is a biologic, e.g., a protein having a molecular weight of between 5-300 kDa. For example, a TWEAK blocking agent may inhibit binding of TWEAK to a TWEAK receptor. Exemplary TWEAK blocking agents, other than antibodies that bind to TWEAK, include antibodies that bind to TWEAK-R and soluble forms of the TWEAK-R (e.g., Fn14) that compete with cell surface TWEAK-R for binding to TWEAK. Other therapeutic agents described herein can also be provided as a pharmaceutical composition, e.g., by standard methods or method described herein.

Administration

The anti-TWEAK antibody can be administered to a subject, e.g., a human subject, by a variety of methods. For many applications, the route of administration is one of: intravenous injection or infusion (IV), subcutaneous injection (SC), intraperitoneally (IP), or intramuscular injection. It is also possible to use intra-articular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration may be directly to a site of inflammation, e.g., a joint or other inflamed site.

The route and/or mode of administration of the antibody can also be tailored for the individual case, e.g., by monitoring the subject, e.g., using tomographic imaging, neurological exam, and standard parameters associated with the particular disorder, e.g., criteria for assessing rheumatoid arthritis.

The antibody can be administered as a fixed dose, or in a mg/kg dose. The dose can also be chosen to reduce or avoid production of antibodies against the anti-TWEAK antibody. Dosage regimens are adjusted to provide the desired response, e.g., a therapeutic response or a combinatorial therapeutic effect. Generally, doses of the anti-TWEAK antibody (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the antibody may be administered via continuous infusion.

A anti-TWEAK antibody dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments. Animal models can also be used to determine a useful dose, e.g., an initial dose or a regimen.

If a subject is at risk for developing an inflammatory disorder or other disorder described herein, the antibody can be administered before the full onset of the disorder, e.g., as a preventative measure. The duration of such preventative treatment can be a single dosage of the antibody or the treatment may continue (e.g., multiple dosages). For example, a subject at risk for the disorder or who has a predisposition for the disorder may be treated with the antibody for days, weeks, months, or even years so as to prevent the disorder from occurring or fulminating.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Devices and Kits for Therapy

Pharmaceutical compositions that include the anti-TWEAK antibody can be administered with a medical device. The device can designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include anti-TWEAK antibody, and can be configured to deliver one or more unit doses of the antibody. The device can be further configured to administer a second agent, e.g., an anti-TNF-α antibody, either as a single pharmaceutical composition that also includes the anti-TWEAK antibody or as two separate pharmaceutical compositions.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

An anti-TWEAK antibody can be provided in a kit. In one embodiment, the kit includes (a) a container that contains a composition that includes the anti-TWEAK antibody, and optionally (b) informational material. The informational material can be descriptive, instructional, marketing or other material that relates to the methods described herein and/or the use of the agents for therapeutic benefit.

In an embodiment, the kit also includes a second agent for treating an inflammatory disorder, e.g., an anti-TNF-α antibody. For example, the kit includes a first container that contains a composition that includes the anti-TWEAK antibody, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-TWEAK antibody, e.g., in a suitable dose, dosage form, or mode of administration (e.g., a dose, dosage form, or mode of administration described herein), to treat a subject who has had or who is at risk for an inflammatory disorder, or other disorder described herein. The information can be provided in a variety of formats, include printed text, computer readable material, video recording, or audio recording, or information that provides a link or address to substantive material, e.g., on the internet.

In addition to the antibody, the composition in the kit can include other ingredients, such as a solvent or buffer, a stabilizer, or a preservative. The antibody can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-TWEAK antibody and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Targeting TWEAK-Expressing Cells

The anti-TWEAK antibodies described herein can be used to target a payload to a TWEAK-expressing cell or to a tissue or other structure associated with TWEAK. For example, the antibodies can be attached to a virus or virus like particle that can deliver an exogenous gene (e.g., for gene therapy) or to a liposome, e.g., a liposome that encapsulates a therapeutic agent or exogenous gene. An exemplary method for using an antibody to target a virus is described in Roux et al. (1989) *Proc Natl Acad Sci USA* (1989) 86:9079-9083. See also, e.g., *Curr Gene Ther.* (2005) 5:63-70 and *Hum Gene Ther.* (2004) 15:1034-1044.

The anti-TWEAK Abs of this invention may also be attached to liposomes containing a therapeutic agent such as a chemotherapeutic agents. Attachment of antibodies to liposomes may be accomplished by any known cross-linking agent such as heterobifunctional cross-linking agents that have been widely used to couple toxins or chemotherapeutic agents to antibodies for targeted delivery. For example, conjugation to liposomes can be accomplished using the carbohydrate-directed cross-linking reagent 4-(4-maleimidophenyl) butyric acid hydrazide (MPBH) (Duzgunes et al. (1992) *J. Cell. Biochem*, Abst. Suppl. 16E 77). Liposomes containing antibodies can also be prepared by well-known methods (See, e.g. DE 3,218,121; Epstein et al. (1985) *Proc. Natl. Acad. Sci. USA*, 82:3688-92; Hwang et al. (1980) *Proc. Natl. Acad. Sci. USA*, 77:4030-34; U.S. Pat. Nos. 4,485,045 and 4,544,545).

Diagnostic Uses

Anti-TWEAK antibodies can be used in a diagnostic method for detecting the presence of a TWEAK, in vitro (e.g., a biological sample, such as tissue, biopsy) or in vivo (e.g., in vivo imaging in a subject). For example, human or effectively human anti-TWEAK antibodies can be administered to a subject to detect TWEAK within the subject. For example, the antibody can be labeled, e.g., with an MRI detectable label or a radiolabel. The subject can be evaluated using a means for detecting the detectable label. For example, the subject can be scanned to evaluate localization of the antibody within the subject. For example, the subject is imaged, e.g., by NMR or other tomographic means.

Examples of labels useful for diagnostic imaging include radiolabels such as $^{131}I$, $^{111}In$, $^{123}I$, $^{99m}Tc$, $^{32}P$, $^{33}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, can also be employed. The protein ligand can be labeled with such reagents using known techniques. For example, see Wensel and Meares (1983) *Radioimmunoimaging and Radioimmunotherapy*, Elsevier, N.Y. for techniques relating to the radiolabeling of antibodies and Colcher et al. (1986) *Meth. Enzymol.* 121: 802-816.

The subject can be "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP0 502 814 A. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents, paramagnetic agents (which primarily alter T1) and ferromagnetic or superparamagnetic agents (which primarily alter T2 response). Chelates (e.g., EDTA, DTPA and NTA chelates) can be used to attach (and reduce toxicity) of some paramagnetic substances (e.g., $Fe^{3+}$, $Mn^{2+}$, $Gd^{3+}$). Other agents can be in the form of particles, e.g., less than 10 μm to about 10 nm in diameter). Particles can have ferromagnetic, anti-ferromagnetic or superparamagnetic properties. Particles can include, e.g., magnetite ($Fe_3O_4$), γ-$Fe_2O_3$, ferrites, and other magnetic mineral compounds of transition elements. Magnetic particles may include one or more magnetic crystals with and without nonmagnetic material. The nonmagnetic material can include synthetic or natural polymers (such as sepharose, dextran, dextrin, starch and the like).

The anti-TWEAK antibodies can also be labeled with an indicating group containing the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American,* 246:78-88 to locate and image TWEAK distribution.

In another aspect, the disclosure provides a method for detecting the presence of TWEAK in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-TWEAK antibody; and (ii) evaluating the sample for the presence of TWEAK, e.g., by detecting formation of a complex between the anti-TWEAK antibody and TWEAK, or by detecting the presence of the antibody or TWEAK. For example, the antibody can be immobilized, e.g., on a support, and retention of the antigen on the support is detected, and/or vice versa. A control sample can be included. A statistically significant change in the formation of the complex in the sample relative to the control sample can be indicative of the presence of TWEAK in the sample. Generally, an anti-TWEAK antibody can be used in applications that include fluorescence polarization, microscopy, ELISA, centrifugation, chromatography, and cell sorting (e.g., fluorescence activated cell sorting).

Example 1

The sequence of the murine P2D10 heavy chain variable domain, with CDRs underlined, is:

```
                                                            (SEQ ID NO:50)
  1 EVQLVESGGG LVRPGGSLKL FCAASGFTFS RYAMSWVRQS PEKRLEWVAE

51 ISSGGSYPYY PDTVTGRFTI SRDNAKNTLY LEMSSLKSED TAMYYCARVL

101 YYDYDGDRIE VMDYWGQGTA VIVSS
```

This is a murine subgroup 3D heavy chain variable domain.

The sequence of the murine P2D10 light chain variable domain, with CDRs underlined, is:

```
                                                            (SEQ ID NO:51)
  1 DVVMTQSPLS LSVSLGDQAS ISCRSSQSLV SSKGNTYLHW YLQKPGQSPK

51 FLIYKVSNRF SGVPDRFSGS GSGTDFTLKI SRVAAEDLGV YFCSQSTHFP

101 RTFGGGTTLE IK
```

This is a murine subgroup 2 kappa light chain.

The following human acceptor frameworks were chosen for huP2D10: Human 56-84m subgroup 3 heavy chain variable domain (NCBI database accession number GI:33318898, Scamurra et al., direct submission). The sequence with CDRs underlined is as follows:

```
                                                          (SEQ ID NO:52)
  1 EVQLVESGGG LVQPGGSLRL SCAASGFTFS SYWMSWVRQA PGKGLEWVAN

51 IKQDGSEKYY VDSVKGRFTI SRDNAKNSLY LQMNSLRAED TAVYYCARDP

101 MTTVVKPSLA TNDYWGQGTL VTVSS
```

The sequence of human K107 subgroup 2 light chain variable domain (NCBI database accession number GI: 21669075, Akahori et al., direct submission), with CDRs underlined is:

```
                                                          (SEQ ID NO: 53)
  1 DVVMTQSPLS LPVTPGEPAS ISCRSSQSLL HSNGYNYLDW YLQKPGQSPQ

51 LLIYLGSNRA SGVPDRFSGS GSGTDFTLKI SRVEAEDVGV YYCMQALQTP

101 LTFGGGTKVE IK
```

In the human acceptor sequences shown, the CDRs (which are underlined) are the same length and canonical classes as those in the muP2D10 variable domains.

Shown below is the alignment of the murine P2D10 (top) and human acceptor 56-84m (bottom) heavy chain variable domains (68.8% identical):

```
  1 EVQLVESGGGLVRPGGSLKLFCAASGFTFSRYAMSWVRQSPEKRLEWVAE 50
    |||||||||||.||||:| ||||||||||.| ||||||.| | |||||
  1 EVQLVESGGGLVQPGGSLRLSCAASGFTFSSYWMSWVRQAPGKGLEWVAN 50

51 ISSGGSYPYYPDTVTGRFTISRDNAKNTLYLEMSSLKSEDTAMYYCARVL 100
    |  ||  || |.| |||||||||||||.|||:|.||:.||||.|||||
 51 IKQDGSEKYYVDSVKGRFTISRDNAKNSLYLQMNSLRAEDTAVYYCARDP 100

101 YYDYDGDRIEVMDYWGQGTAVIVSS 125 (SEQ ID NO:54)
         :     |||||| | |||
101 MTTVVKPSLATNDYWGQGTLVTVSS 125 (SEQ ID NO:55)
```

Shown below is the alignment of the murine P2D10 (top) and human acceptor K107 light (bottom) chain variable domains (75.9% identical):

```
  1 DVVMTQSPLSLSVSLGDQASISCRSSQSLVSSKGNTYLHWYLQKPGQSPK 50
    ||||||||||| |. |: |||||||||.| || || |||||||||||.
  1 DVVMTQSPLSLPVTPGEPASISCRSSQSLLHSNGYNYLDWYLQKPGQSPQ 50

51 FLIYKVSNRFSGVPDRFSGSGSGTDFTLKISRVAAEDLGVYFCSQSTHFP 100
    |||  |||  ||||||||||||||||||||||||| .|||:|  | .  |
 51 LLIYLGSNRASGVPDRFSGSGSGTDFTLKISRVEAEDVGVYYCMQALQTP 100

101 RTFGGGTTLEIK 112 (SEQ ID NO:56)
    ||||||.|||
101 LTFGGGTKVEIK 112 (SEQ ID NO:57)
```

There are two versions of huP2D10 light chain (L1 and L2). The antibody huP2D10-1 refers to an antibody that includes huP2D10 H1 and huP2D10 L1. The antibody huP2D10-2 refers to an antibody that includes huP2D10 H1 and huP2D10 L2.

Shown below is the alignment of the 56-84m human acceptor (top) and the huP2D10 H1 heavy chain (bottom) variable domain:

```
  1 EVQLVESGGGLVQPGGSLRLSCAASGFTFSSYWMSWVRQAPGKGLEWVAN 50
    |||||||||||||||||||||||||||||| | ||||||||||||||||
  1 EVQLVESGGGLVQPGGSLRLSCAASGFTFSRYAMSWVRQAPGKGLEWVAE 50
```

```
 51 IKQDGSEKYYVDSVKGRFTISRDNAKNSLYLQMNSLRAEDTAVYYCARDP 100
    |  || || |.| ||||||||||||||||||||||||||||||||||
 51 ISSGGSYPYYPDTVTGRFTISRDNAKNSLYLQMNSLRAEDTAVYYCARVL 100

101 MTTVVKPSLATNDYWGQGTLVTVSS 125 (SEQ ID NO:58)
            :   |||||||||||||||
101 YYDYDGDRIEVMDYWGQGTLVTVSS 125 (SEQ ID NO:59)
```

CDRs are underlined. The huP2D10 heavy chain is a straight CDR graft (i.e., there are no back mutations in the framework).

Shown below is the alignment of the K107 human kappa acceptor (top) and the huP2D10 L1 light chain (bottom) variable domain:

```
  1 DVVMTQSPLSLPVTPGEPASISCRSSQSLLHSNGYNYLDWYLQKPGQSPQ 50
    |||||||||||||||||||||||||||||.| || ||  |||||||||||
  1 DVVMTQSPLSLPVTPGEPASISCRSSQSLVSSKGNTYLHWYLQKPGQSPQ 50

51 LLIYLGSNRASGVPDRFSGSGSGTDFTLKISRVEAEDVGVYYCMQALQTP 100
    |||  |||   ||||||||||||||||||||||||||||||||:| |.  
 51 fLIYKVSNRFSGVPDRFSGSGSGTDFTLKISRVEAEDVGVYfCSQSTHFP 100

101 LTFGGGTKVEIK 112 (SEQ ID NO:60)
    ||||||||||||
101 RTFGGGTKVEIK 112 (SEQ ID NO:61)
```

CDRs are underlined. The huP2D10 L1 light chain has two back mutations that are indicated in lower case in the framework shown above: L46F in FR2 and Y87F in FR3.

Shown below is the alignment of the K107 human acceptor (top) and the huP2D10 L2 light chain (bottom) variable domain:

```
  1 DVVMTQSPLSLPVTPGEPASISCRSSQSLLHSNGYNYLDWYLQKPGQSPQ 50
    |||||||||||||||||||||||||||||.| || ||  |||||||||||
  1 DVVMTQSPLSLPVTPGEPASISCRSSQSLVSSKGNTYLHWYLQKPGQSPQ 50

51 LLIYLGSNRASGVPDRFSGSGSGTDFTLKISRVEAEDVGVYYCMQALQTP 100
    |||| |||  ||||||||||||||||||||||||||||||||||:|    
 51 LLIYKVSNRFSGVPDRFSGSGSGTDFTLKISRVEAEDVGVYYCSQSTHFP 100

101 LTFGGGTKVEIK 112 (SEQ ID NO:62)
    ||||||||||||
101 RTFGGGTKVEIK 112 (SEQ ID NO:63)
```

CDRs are underlined. The huP2D10 L2 light chain is a straight CDR graft (without back mutations in the framework).

This is an exemplary amino acid sequence of the mature huP2D10 H1 IgG1 heavy chain:

(SEQ ID NO: 64)

```
  1 EVQLVESGGG LVQPGGSLRL SCAASGFTFS RYAMSWVRQA PGKGLEWVAE

51 ISSGGSYPYY PDTVTGRFTI SRDNAKNSLY LQMNSLRAED TAVYYCARVL

101 YYDYDGDRIE VMDYWGQGTL VTVSSASTKG PSVFPLAPSS KSTSGGTAAL

151 GCLVKDYFPE PVTVSWNSGA LTSGVHTFPA VLQSSGLYSL SSVVTVPSSS

201 LGTQTYICNV NHKPSNTKVD KKVEPKSCDK THTCPPCPAP ELLGGPSVFL

251 FPPKPKDTLM ISRTPEVTCV VVDVSHEDPE VKFNWYVDGV EVHNAKTKPR

301 EEQYNSTYRV VSVLTVLHQD WLNGKEYKCK VSNKALPAPI EKTISKAKGQ

351 PREPQVYTLP PSRDELTKNQ VSLTCLVKGF YPSDIAVEWE SNGQPENNYK
```

```
401 TTPPVLDSDG SFFLYSKLTV DKSRWQQGNV FSCSVMHEAL HNHYTQKSLS

451 LSPG
```

Kabat numbering for the $V_H$ segment of the heavy chain variable domain (SEQ ID NO:65) is shown below:

```
Kabat No.  1234567890 1234567890 1234567890 1234567890 1234567890
hP2D10     EVQLVESGGG LVQPGGSLRL SCAASGFTFS RYAMSWVRQA PGKGLEWVAE Kabat No.  12a3456789 0123456789 0123456789 012abc3456 78901234
hP2D10     ISSGGSYPYY PDTVTGRFTI SRDNAKNSLY LQMNSLRAED TAVYYCAR
```

This is an exemplary amino acid sequence of the mature huP2D10 L1 light chain:

```
                                                    (SEQ ID NO: 66)
  1 DVVMTQSPLS LPVTPGEPAS ISCRSSQSLV SSKGNTYLHW YLQKPGQSPQ

51 FLIYKVSNRF SGVPDRFSGS GSGTDFTLKI SRVEAEDVGV YFCSQSTHFP

101 RTFGGGTKVE IKRTVAAPSV FIFPPSDEQL KSGTASVVCL LNNFYPREAK

151 VQWKVDNALQ SGNSQESVTE QDSKDSTYSL SSTLTLSKAD YEKHKVYACE

201 VTHQGLSSPV TKSFNRGEC
```

Kabat numbering for this $V_L$ segment is shown below (SEQ ID NO:67):

```
Kabat No.  1234567890 1234567890 1234567abc de89012345 6789012345
hP2D10     DVVMTQSPLS LPVTPGEPAS ISCRSSQSLV SSKGNTYLHW YLQKPGQSPQ Kabat No.  6789012345 6789012345 6789012345 6789012345 6789012345
hP2D10     FLIYKVSNRF SGVPDRFSGS GSGTDFTLKI SRVEAEDVGV YFCSQSTHFP
```

This is an exemplary amino acid sequence of the mature huP2D10 L2 light chain:

```
                                                    (SEQ ID NO: 68)
  1 DVVMTQSPLS LPVTPGEPAS ISCRSSQSLV SSKGNTYLHW YLQKPGQSPQ

51 LLIYKVSNRF SGVPDRFSGS GSGTDFTLKI SRVEAEDVGV YYCSQSTHFP

101 RTFGGGTKVE IKRTVAAPSV FIFPPSDEQL KSGTASVVCL LNNFYPREAK

151 VQWKVDNALQ SGNSQESVTE QDSKDSTYSL SSTLTLSKAD YEKHKVYACE

201 VTHQGLSSPV TKSFNRGEC
```

Kabat numbering for this $V_L$ segment is shown below (SEQ ID NO:69):

```
Kabat No.  1234567890 1234567890 1234567abc de89012345 6789012345
hP2D10     DVVMTQSPLS LPVTPGEPAS ISCRSSQSLV SSKGNTYLHW YLQKPGQSPQ Kabat No.  6789012345 6789012345 6789012345 6789012345 6789012345
hP2D1      LLIYKVSNRF SGVPDRFSGS GSGTDFTLKI SRVEAEDVGV YFCSQSTHFP
```

Example 2

The blocking monoclonal antibody to TWEAK, mP2D10, significantly reduced clinical severity in models of multiple sclerosis and stroke. The pharmacokinetics (PK) of anti-TWEAK monoclonal antibody, mP2D10, following intravenous (IV) administration were modeled.

mP2D10 was administered to mice at 1, 10 or 100 mg/kg via IV injection. Serum concentrations of mP2D10 was determined using ELISA. The concentration-time PK profile was analyzed using a two-compartment model with first-order elimination or Michaelis-Menten elimination from the central compartment with a volume of V1. The rate constants between the two compartments were K12 (exiting compartment 1 to 2) and K21 (exiting compartment 2 to 1). For the first-order elimination model, the elimination rate constant was K10. For the Michaelis-Menten elimination model, the drug was cleared at the rate of Vm*C1/(Km+C1), in which, C1 was mP2D10 in the concentration in the central compartment, Vm and Km were constants. The data were fitted with ADAPT II software (D'Argenio, D. Z. and A. Schumitzky. *ADAPT II User's Guide. Pharmacokinetic/Pharmacodynamic Systems Analysis Software*. Biomedical Simulations Resource, Los Angeles, 1997.) using the Maximum Likelihood estimation procedure.

For the two-compartment linear elimination model, V1 was 23.2 mL/kg, K10 was 0.0096 h−1, the K12 was 2.501 and K21 was 1.053. The area under curve (AIC) value was 298 and the Schwarz value was 304.2. For the two-compartment non-linear elimination model, the V1 was 0.0235. The Vm was 9.22 mg/kg/hr, the Km was 484.2 μg/mL. The K12 was 2.348 h−1, and the K21 was 0.966 h−1. The AIC value was 269 and the Schwarz value was 276. The PK of mP2D10 was better predicted by a non-linear model than a linear model.

The concentration-time profiles of mP2D 0 were better predicted by a two-compartment model with Michaelis-Menten elimination than with first order elimination.

Those skilled in the art will recognize, or be able to ascertain using no more than routine experimentation, many equivalents of the specific embodiments described herein described herein.

What is claimed:

1. A humanized antibody that binds to human TWEAK or an antigen binding fragment thereof comprising:
   a) heavy chain variable domain complementarity determining regions (CDRs), wherein
   CDR1 comprises the amino acid sequence set forth in SEQ ID NO:4;
   CDR2 comprises the amino acid sequence set forth in SEQ ID NO:5; and
   CDR3 comprises an amino acid sequence set forth in SEQ ID NO:6, or SEQ ID NO:7; and
   b) light chain variable domain CDRs, wherein
   CDR1 comprises an amino acid sequence set forth in SEQ ID NO:11;
   CDR2 comprises an amino acid sequence set forth in SEQ ID NO:13; and
   CDR3 comprises an amino acid sequence set forth in SEQ ID NO:15.

2. The humanized antibody or antigen binding fragment of claim 1, wherein the heavy chain CDRS1-3 have the amino acid sequences set forth in SEQ ID NO:1, SEQ ID NO:2, and SEQ ID NO:3, respectively.

3. The humanized antibody or antigen binding fragment of claim 1, wherein the light chain CDRS1-3 have the amino acid sequences set forth in SEQ ID NO:8, SEQ ID NO:9, and SEQ ID NO:10, respectively.

4. A humanized antibody that binds to human TWEAK or an antigen binding fragment thereof comprising heavy chain CDRS1-3 that have the amino acid sequences set forth in SEQ ID NO:1, SEQ ID NO:2, and SEQ ID NO:3, respectively and light chain CDRS1-3 that have the amino acid sequences set forth in SEQ ID NO:8, SEQ ID NO:9, and SEQ ID NO:10, respectively.

* * * * *